United States Patent
Choi et al.

[19]

[11] Patent Number: 6,011,044
[45] Date of Patent: Jan. 4, 2000

[54] PYRROLO [3,2-C] QUINOLINE DERIVATIVES CONTAINING HALOALKOXY GROUP AND PHARMACEUTICALLY ACCEPTABLE SALTS THEREOF

[75] Inventors: Joong-Kwon Choi; Sung-Soo Kim; Eul-Kyun Yum; Seung-Kyu Kang; Yea-Kang Yoo; Hyae-Gyeong Cheon; Hyo-Jung Kim, all of Taejon-si, Rep. of Korea

[73] Assignee: Korea Research Institute of Chemical Technology, Taejon-si, Rep. of Korea

[21] Appl. No.: 09/130,954

[22] Filed: Aug. 7, 1998

[30] Foreign Application Priority Data

Aug. 13, 1997 [KR] Rep. of Korea ............ 97-38512

[51] Int. Cl.[7] .................. A61K 31/47; C07D 471/04
[52] U.S. Cl. .................. 514/292; 546/84
[58] Field of Search .................. 546/84; 514/292

[56] References Cited

U.S. PATENT DOCUMENTS 5,051,508  9/1991  Brown ........................ 546/84

FOREIGN PATENT DOCUMENTS 0441036  8/1991  European Pat. Off. .

OTHER PUBLICATIONS

Leach et al., "Reversible Inhibitors of the Gastric ($H^+/K^+$)–ATPase. 2.1–Arylpyrrolo [[3, 2–c] quinolines: Effect of the 4–Substituent ", J. Med.Chem. 1992, 35, 1845–1852.

*Primary Examiner*—Evelyn Mei Huang
*Attorney, Agent, or Firm*—Dilworth & Barrese

[57] ABSTRACT

The present invention relates to a novel pyrrolo[3,2-c] quinoline derivatives containing haloalkoxy group, represented by Formula I, their pharmaceutically acceptable salts; process for preparation thereof; and pharmaceutical composition thereof for treating gastric ulcer.

Formula I

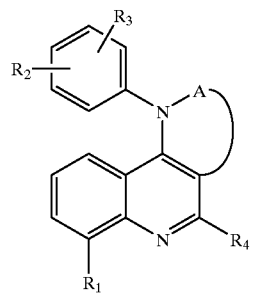

in which $R_1$ is haloalkoxy group of $C_1$–$C_6$ including trifluoromethoxy, difluoromethoxy and trifluoroethoxy group.

$R_2$ and $R_3$, which are the same or different, are each hydrogen, halogen, hydroxy, benzyloxy, alkyl group of $C_1$–$C_6$, alkoxy group of $C_1$–$C_6$.

A is —$CH_2$—$CH_2$— or —CH=CH—, and $R_4$ is hydrogen, halogen, amino, alkylamino group of $C_1$–$C_6$, and $NH(CH_2)_nOH$ in which n is 1–6. Pyrrolo [3,2-c]quinoline derivatives having haloalkoxy group, and their pharmaceutically acceptable salts, which reversibly inhibit gastric acid secretion of mammal, are usefully utilized for gastric ulcer therapeutics.

16 Claims, No Drawings

PYRROLO [3,2-C] QUINOLINE DERIVATIVES CONTAINING HALOALKOXY GROUP AND PHARMACEUTICALLY ACCEPTABLE SALTS THEREOF

FIELD OF THE INVENTION

The present invention relates to a novel pyrrolo[3,2-c]quinoline derivatives containing haloalkoxy group, their pharmaceutically acceptable salts; process for preparation thereof; and pharmaceutical composition thereof for treating gastric ulcer. More particularly, the present invention relates to novel pyrrolo[3,2-c]quinoline derivatives, as represented by Formula I, in which $R_1$ is haloalkoxy group, which reversibly inhibit gastric acid secretion of mammal; their salts; and process for preparation thereof; pharmaceutical composition thereof is effective for treating gastric ulcer.

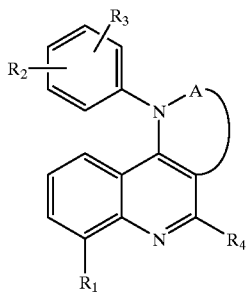

Formula I in which $R_1$ is haloalkoxy group of $C_1$–$C_6$ including trifluoromethoxy, difluoromethoxy and trifluoroethoxy group.

$R_2$ and $R_3$, which are the same or different, are each hydrogen, halogen, hydroxy, benzyloxy, alkyl group of $C_1$–$C_6$, alkoxy group of $C_1$–$C_6$.

A is —CH$_2$—CH$_2$— or —CH=CH—, and $R_4$ is hydrogen, halogen, amino, alkylamino group of $C_1$–$C_6$, and NH(CH$_2$)$_n$OH in which n is 1–6.

So far, benzimidazole derivatives containing pyridine as represented by the Omeprazole, commercial name, have been commonly used for inhibitor of gastric acid secretion. Benzimidazole derivatives containing pyridine have displayed a prominent remedial result, but have raised a problem in long term administration because of their irreversible reaction mechanism. That is, there have been sustained effect of medicine after stopping administration or side effect of thickening stomach wall by administration, etc.

In addition, quinoline derivatives have been known as the inhibitor of gastric acid secretion of mammal, and there have been attempts to develop them as a reversible inhibitor of gastric acid secretion. [European Patent No. 87-307824.0; U.S. Pat. No. 5,362,743; PCT KR 94-29274; European Patent No. 89-301801.0; European Patent No. 87-301805.1; European Patent No. 89-301802.8; European Patent No. 88-306583.1; PCT KR 97-00074; KP 96-38314; KP 97-30692; KP 97-30693; J. Med. Chem., 1992, 35, 1845–1852; J. Med. Chem., 1992, 35, 3413–3422; and J. Med. Chem., 1995, 38, 2748–2762].

For example, European Patent No. 88-306583.1 describes pyrrolo[3,2-c]quinoline derivatives of the following structure.

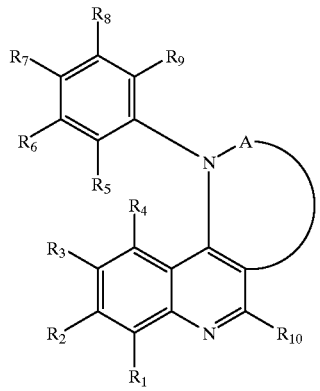

Formula II in which A is —CH$_2$—CH$_2$—, —CH=CH— or —(CH$_2$)$_3$—, $R_1$ to $R_4$ are each hydrogen, halogen, alkyl group of $C_1$–$C_4$, alkoxy group of $C_1$–$C_6$, phenyl group, alkylthio group of $C_1$–$C_6$, alkanoyl group of $C_1$–$C_4$, alkylamino group of $C_1$–$C_6$, dialkylamino group of $C_1$–$C_6$, trifluoromethyl or nitro group.

$R_3$ to $R_9$ are each alkyl of $C_1$–$C_6$, alkoxy group of $C_1$–$C_6$, alkylthio group of $C_1$–$C_6$, halogen, cyano, amino, hydroxy, carbamoyl, carbonyl, alkanoyl group of $C_1$–$C_6$, trifluoromethyl or nitro group.

$R_{10}$ is hydrogen, halogen, alkyl group of $C_1$–$C_6$, alkoxy group of $C_1$–$C_6$, alkylthio group of $C_1$–$C_6$, hydroxy group, —CH$_2$OH, NR$_{11}$R$_{12}$ or NH(CH$_2$)$_n$OH in which n is 0 to 4.

Above-mentioned literature described that compound of Formula II and their salts play a role as the inhibitor of gastric acid secretion by inhibiting H$^+$/K$^+$-ATPase enzyme in stomach, and are useful for treating gastric disease in mammal, particularly in human.

Another literature (J. Med. Chem., 1992, 35, 1845–1852) about 1-arylpyrrolo[3,2-c]quinoline derivatives as a reversible inhibitor of gastric acid secretion, described particularly effect of substituent $R_{10}$.

There have been some reports of 1-arylpyrrolo[3,2-c]quinoline derivatives in which $R_1$ is substituted with alkoxy group, but no report with haloalkoxy group. We, the inventors of the present invention, synthesized novel 1-aryl-6-haloalkoxypyrrolo[3,2-c]quinoline derivatives in which $R_1$ was substituted haloalkoxy group, and found that they showed excellent effect on gastric ulcer by reversibly inhibiting the gastric acid secretion.

SUMMARY OF THE INVENTION

The present invention has an object of providing novel pyrrolo[3,2-c]quinoline derivatives and their pharmaceutically acceptable salts, as represented by Formula I. That is, the present invention is to provide novel pyrrolo[3,2-c]quinoline derivatives, in which $R_1$ is haloalkoxy group, as represented by Formula I.

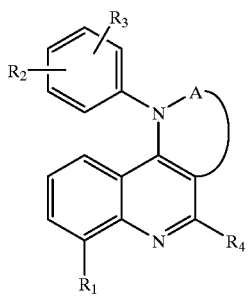

Formula I in which $R_1$ is haloalkoxy group of $C_1-C_6$ including trifluoromethoxy, difluoromethoxy and trifluoroethoxy group.

$R_2$ and $R_3$, which are the same or different, are each hydrogen, halogen, hydroxy, benzyloxy, alkyl group of $C_1-C_6$, and alkoxy group of $C_1-C_6$.

A is —$CH_2$—$CH_2$— or —CH=CH—, and $R_4$ is hydrogen, halogen, amino, alkylamino group of $C_1-C_6$, and $NH(CH_2)_nOH$ in which n is 1–6.

Compound of Formula I in which $R_1$ is selected from trifluoromethoxy, difluoroethoxy or β,β,β-trifluoroethoxy, $R_2$ or $R_3$ is selected from hydrogen, methyl, methoxy, hydroxy or fluoro and $R_4$ is selected from methylamino or $NH(CH_2)_nOH$, has most preferable effect.

The present invention has an another object to provide pharmaceutical composition containing pyrrolo[3,2-c] quinoline derivatives and their pharmaceutically acceptable salts in which $R_1$ is haloalkoxy group, as represented by Formula I, as an effective ingredient.

The present invention has an another object to provide a process for preparation of pyrrolo[3,2-c]quinoline derivatives and their salts in which $R_1$ is haloalkoxy group, as represented by Formula I.

The present invention has another object to provide the use of pharmaceutical composition containing pyrrolo[3,2-c]quinoline derivatives and their salts as an effective ingredient, represented by Formula I, as reversible inhibitor of gastric acid secretion and medicine for gastric ulcer.

DETAILED DESCRIPTION OF THE INVENTION

The present invention of pyrrolo[3,2-c]quinoline derivatives in which $R_1$ is haloalkoxy group, can be prepared by the following process.

In the following Scheme I, 1-aryl-4-oxo-6-haloalkoxy-2,3,4,5-tetrahydropyrrolo[3,2-c]quinoline of structure ($V_a$) can be prepared by reacting aniline in which benzene ring has substituent $R_2$ and $R_3$, of structure (IV) with 4-oxo-6-haloalkoxyfuro[3,2-c]quinoline compound (III), which can be synthesized by condensation of diethyl 2-ethoxyethylmalonate and aniline, substituted in ortho-position with haloalkoxy group, of structure (II).

1-Aryl-4-oxo-6-haloalkoxy-4,5-tetrahydropyrrolo[3,2-c] quinoline derivatives in which A is unsaturated —CH=CH—, of structure ($V_b$) can be prepared by oxidizing the 1-aryl-4-oxo-6-haloalkoxy-2,3,4,5-dihydropyrrolo [3,2-c]quinoline of structure ($V_a$) in the presence of Pd catalyst, etc.

As shown in the following Scheme II, pyrrolo[3,2-c] quinoline derivatives of structure ($I_a$) in which A is saturated —$CH_2$—$CH_2$—, can be prepared by chlorinating the 4-position of structure ($V_a$), then substituting chlorine in 4-position with $R_4$.

And, as shown in the following Scheme III, pyrrolo[3,2-c]quinoline derivatives of Structure($I_a$) containing haloalkoxy group in which A is unsaturated —CH=CH—, can be prepared by chlorinating the 4-position of compound ($V_b$), then substituting chlorine in 4-position $R_4$.

Process for preparation of pyrrolo[3,2-c]quinoline derivatives having haloalkoxy group, of Formula I, will now be described in detail with reference to the Schemes showing embodiments thereof.

In the process for preparation of pyrrolo[3,2-c]quinoline derivatives of Formula I, intermediate may be different according that A is —$CH_2$—$CH_2$— or —CH=CH— in the Formula I.

Also, process for preparation of pyrrolo[3,2-c]quinoline derivatives may be different in accordance with their substituents. Firstly, process for preparation of intermediate, used for preparing the pyrrolo[3,2-c]quinoline derivatives, will now be described in detail with reference to the Scheme I, as follows:

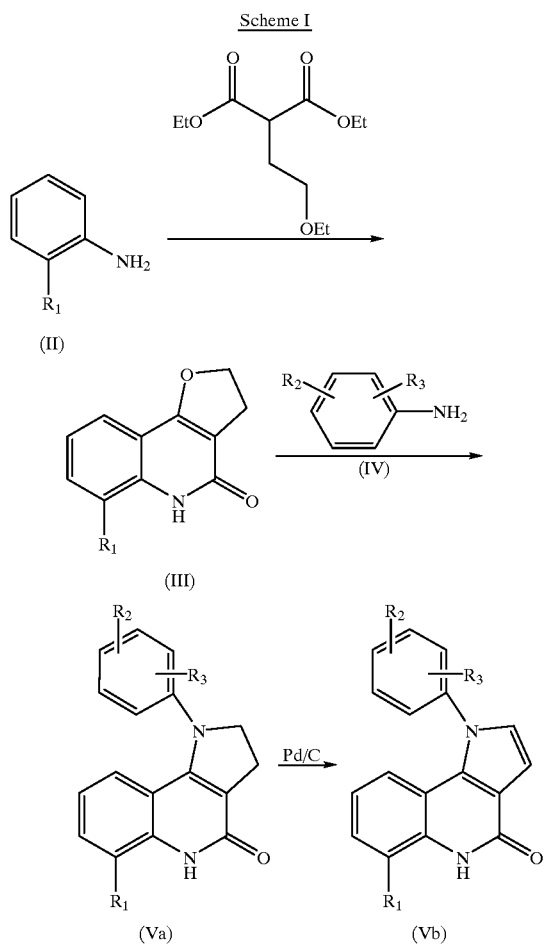

Scheme I in which substituents $R_1$, $R_2$, $R_3$ and $R_4$ are each defined as above.

1) 4-oxo-6-haloalkoxy-2,3,4,5-tetrahydrofuro[3,2-c] quinoline compound (III) can be prepared by condensation of aniline of structure (II), substituted in ortho-position with haloalkoxy group, and diethyl 2-ethoxyethylmalonate by the common method [J. Chem. Soc., 1995, 4284; J. Med. Chem., 1992, 35, 1845]. In this reaction, it is preferable that diethyl 2-ethoxyethylmalonate is used about 1–3 equivalents to the above aniline compound, that diphenyl ether is used as reaction solvent, and that reaction is maintained at 200–270° C. for 24–72 hours. Additionally, rate and yield of reaction can be improved by removing the alcohol formed during the reaction with Dean-Stark apparatus.

2) 1-Aryl-4-oxo-6-haloalkoxy-2,3,4,5-tetrahydropyrrolo [3,2-c]quinoline compound ($V_a$) can be synthesized by the process for preparation, described in the literature [KP 96-16624, PCT KR 97-00074]. Compound ($V_a$), that is, can be prepared by refluxing the 4-oxo-6-haloalkoxy-2,3,4,5-tetrahydrofuro[3,2-c]quinoline compound (III) with the above aniline compound (IV), in which benzene ring has substituent $R_2$ and $R_3$, under inert atmosphere, such as nitrogen. In the reaction, 1–3 equivalents of aniline compound, as represented by structure (IV), is generally used. Reaction is finished at the time of all the 4-oxo-6-haloalkoxy-2,3,4,5-tetrahydrofuro[3,2-c]quinoline compound consumed, and it can be easily observed by the thin layer chromatography(TLC).

According to the above reaction, solvent is preferably selected from alcoholic solvents of which boiling point is 150–280° C., such as phenol, ethylene glycol, diethylene glycol, polyethylene glycol, and so on. It is preferable that reaction is maintained at 150–280° C. for 7–20 hours and carried out under inert atmosphere, such as nitrogen. If the reaction is carried out under atmosphere including oxygen, oxidized compound can be formed as by-product. In addition, using pressure vessel, formation of by-product can be reduced and the rate of reaction can be improved.

3) 1-Aryl-4-oxo-6-haloalkoxy-4,5-dihydropyrrolo[3,2-c] quinoline compound ($V_b$) in which A is unsaturated —CH=CH—, can be prepared by oxidizing the 1-aryl-4-oxo-6-haloalkoxy-2,3,4,5-tetrahydropyrrolo[3,2-c] quinoline compound ($V_a$) in the presence of oxidant. Pd catalyst is used favorably as an oxidant, and Pd/C(10% or 5%) is generally used. It is preferable that diphenyl ether is used for reaction solvent, and that reaction is maintained at 150–250° C. for 3–10 hours.

Compounds of structure ($V_a$) and ($V_b$), each obtained by the above reaction, can be used as intermediates for preparing the pyrrolo[3,2-c]quinoline derivatives according to the present invention. Process for preparation of pyrrolo[3,2-c] quinoline derivatives with above intermediates according to the present invention is depicted in Scheme II and III, as follows.

Scheme II

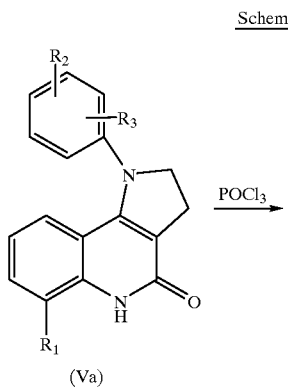

(Va)

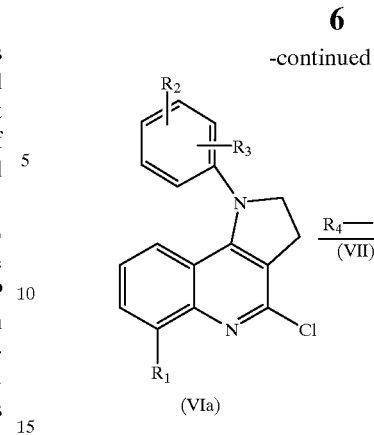

(VIa)      (Ia)

in which substituents $R_1$, $R_2$, $R_3$ and $R_4$ are each defined as above.

1) 1-Aryl-4-chloro-6-haloalkoxy-2,3-dihydropyrrolo[3,2-c]quinoline compound ($VI_a$) can be prepared by chlorinating the 1-aryl-4-oxo-6-haloalkoxy-2,3,4,5-tetrahydropyrrolo[3,2-c]quinoline compound ($V_a$).

According to the above reaction, as shown in Scheme II, it is preferable that chlorinating reagent is selected from phosphoryl chloride, thionyl chloride or oxalic chloride and used about 1–10 equivalents to the compound ($V_a$). Preferably, the reaction solvent is selected from organic halogen solvent such as 1,2-dichloroethane or chloroform, and the reaction can also be carried out under neat condition. It is preferable that the reaction is maintained at 70–150° C. for 1–5 hours. The reaction is finished at the time of all the compound ($V_a$) and it can be easily observed by the TLC.

2) Pyrrolo[3,2-c]quinoline derivatives in which $R_1$ is haloalkoxy group, as represented by structure ($I_a$), can be obtained by reacting the compound ($VI_a$) and (VII). According to this reaction, it is preferable that the compound (VII) is used about 1–10 equivalents to compound ($VI_a$), and that reaction solvent is selected from alcoholic solvent, such as water, ethanol, phenol and ethylene glycol, etc. And, the reaction can be carried out under neat condition, too. It is preferable that the reaction is maintained at 70–200° C. for 5–15 hours. The reaction is finished at the time of all the compound ($VI_a$) being consumed, and it can be easily observed by the TLC. The rate of reaction can be increased by using pressure vessel.

In addition, pyrrolo[3,2-c]quinoline derivatives according to the present invention in which A is unsaturated —CH=CH—, can be prepared by the procedure of the following Scheme III using 1-aryl-4-oxo-6-haloalkoxy-4,5-dihydropyrrolo[3,2-c]quinoline compound ($V_b$).

Scheme III

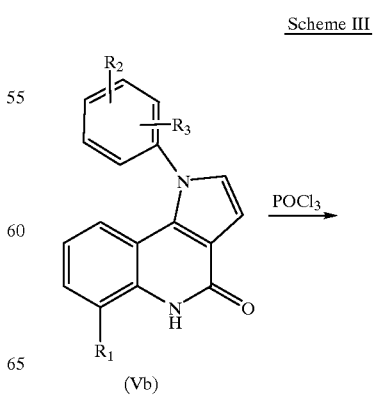

(Vb)

-continued

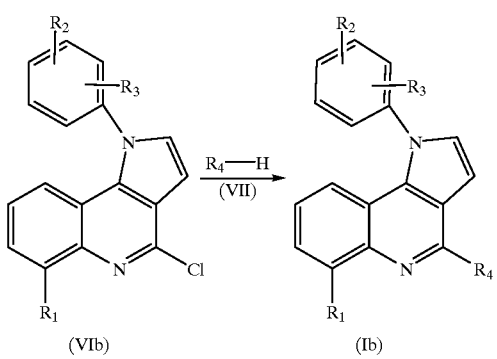

(VIb)  (Ib)

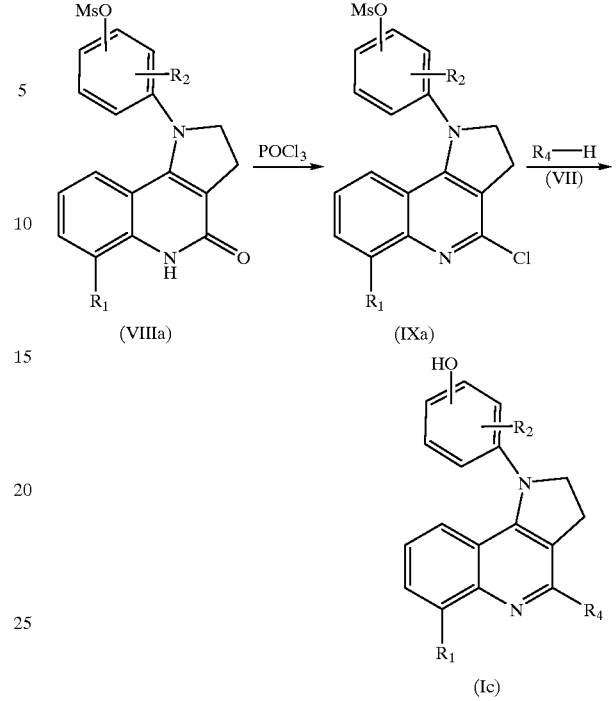

(VIIIa)  (IXa)

(Ic)

in which substituents $R_1$, $R_2$, $R_3$ and $R_4$ are each defined as above.

Process for preparation of pyrrolo[3,2-c]quinoline derivatives containing the substituted haloalkoxy group in 6-position, as shown in structure ($I_b$), is depicted in the Scheme III, is prepared by reacting the compound (VII) with 1-aryl-4-chloro-6-haloalkoxypyrrolo[3,2-c]quinoline compound ($VI_b$) obtained by chlorination of 1-aryl-4-oxo-6-haloalkoxy-4,5-dihydropyrrolo[3,2-c]quinoline of structure ($V_b$). Path and condition of the reaction, as represented by Scheme III, are the same as in the Scheme II.

In addition, among the pyrrolo[3,2-c]quinoline derivatives containing haloalkoxy group of Formula I, pyrrolo[3,2-c]quinoline derivatives in which $R_3$ is hydroxy is prepared by protecting the hydroxy group of 1-aryl-4-oxo-6-haloalkoxy-2,3,4,5-tetrahydropyrrolo[3,2-c]quinoline compound ($V_c$) with protecting group, such as methane-sulfonyl, toluenesulfonyl and so on, especially methanesulfonyl, then reacting it by the same procedures of Scheme II and III. In case that methanesulfonyl group is used as hydroxy protecting group will be described in detail with the reference of the following Scheme IV. Although the foregoing refers to protecting group for hydroxy, it will be understood that the methanesulfonyl is not so limited and familiar to those ordinary skilled in the art.

Scheme IV

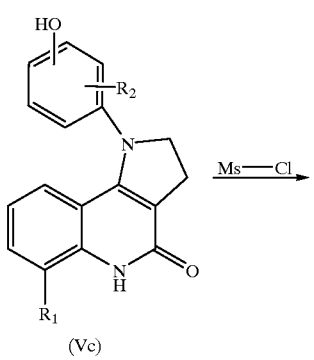

(Vc)

in which substituents $R_1$, $R_2$ and $R_3$ are each defined as above.

1) 1-Aryl-4-oxo-6-haloalkoxy-2,3,4,5-tetrahydropyrrolo[3,2-c]quinoline compound ($VIII_a$) in which hydroxy group is protected with methanesulfonyl, can be obtained by reacting the methanesulfonyl chloride with 1-aryl-4-oxo-6-haloalkoxy-2,3,4,5-tetrahydropyrrolo[3,2-c]quinoline compound ($V_c$) in which $R_3$ is hydroxy. In this reaction, it is preferable that methanesulfonyl chloride is used about 1–1.5 equivalents to the compound ($V_c$). Preferably, dichloromethane is used for reaction solvent and base is selected from triethylamine, pyridine and so on. And, it is preferable that the reaction is maintained at −45–0° C. for 3–7 hours. The reaction is finished at the time of all the compound ($V_c$) being consumed, and it can be easily observed by the TLC.

2) Haloalkoxypyrrolo[3,2-c]quinoline compound ($I_c$) according to the present invention is prepared by reacting the compound (VII) with compound ($IX_a$) obtained by chlorinating the compound ($VIII_a$). Path and condition of this reaction are same as those of the Scheme II and III.

In addition, pyrrolo[3,2-c]quinoline derivatives in which $R_3$ is hydroxy and A is unsaturated —CH=CH—, according to the present invention is prepared by chlorinating the compound ($VIII_b$) in the 4-position, obtained by oxidizing the compound ($VIII_a$), 1-aryl-4-oxo-6-haloalkoxy-2,3,4,5-tetrahydropyrrolo[3,2-c]quinoline compound, then substituting chlorine in the 4-position with $R_4$ of the compound (VII), as shown in the following Scheme V.

Scheme V

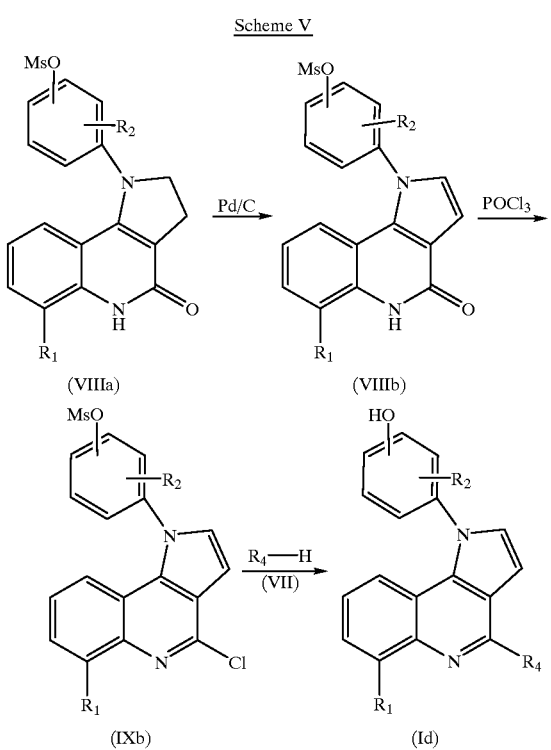

in which $R_1$, $R_2$ and $R_4$ are each defined as above.

1) Compound (VIII$_b$) can be prepared by oxidizing the compound (VIII$_a$), 1-aryl-4-oxo-6-haloalkoxy-2,3,4,5-tetrahydropyrrolo[3,2-c]quinoline compound. The most preferred catalyst is Pd/C(10% or 5%), and the preferred reaction solvent is diphenyl ether. Preferably, reaction is maintained at 150–250° C. for 3–10 hours.

2) It is same as above reaction of Scheme II and III that haloalkoxypyrrolo[3,2-c]quinoline derivatives of structure (I$_d$) according to the present invention is prepared by reacting the compound (VII) with the compound (IX$_b$), obtained by chlorinating the compound (VIII$_b$).

In addition, haloalkoxypyrrolo[3,2-c]quinoline derivatives in which A is unsaturated —CH=CH—, specially A is unsaturated —CH=CH— and $R_4$ is alkylamino(NHR$_5$), may be prepared by oxidizing pyrrolo[3,2-c]quinoline derivatives in which A is saturated —CH$_2$—CH$_2$—, as shown in the following Scheme VI.

Scheme VI

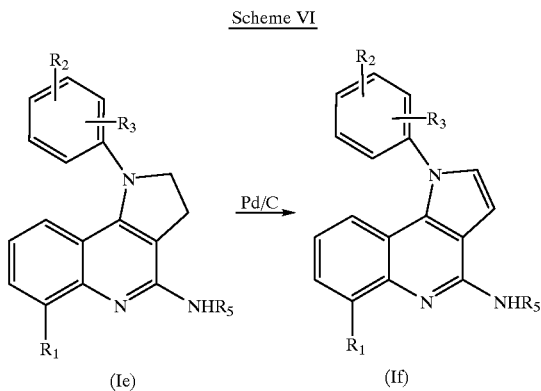

in which substituents $R_1$, $R_2$ and $R_3$ are each defined as above, and $R_5$ is alkyl of $C_1$–$C_6$.

In the above reaction, the most preferred catalyst is Pd/C(10% or 5%) and the preferred reaction solvent is diphenyl ether. The reaction is preferably maintained at 150–250° C. for 3–10 hours, and it is finished at the time of all the starting material being consumed.

2-Haloalkoxy aniline, used as starting material in the process for preparation according to the present invention, can be easily purchased or synthesized from 2-chloronitrobenzene, as shown in the following Scheme VII.

Scheme VII

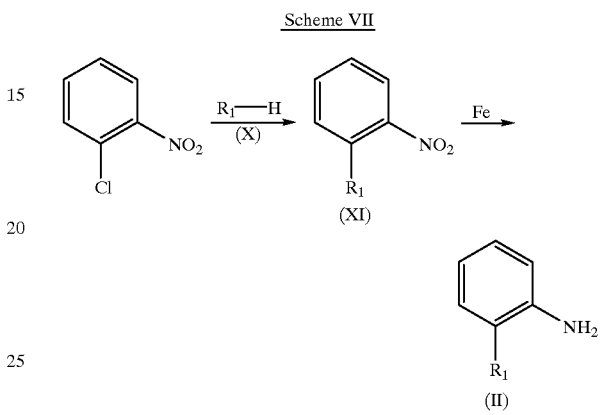

in which $R_1$ is defined as above.

1) Nitrobenzene compound (XI), having haloalkoxy group ($R_1$), can be prepared by reacting the 2-chloronitrobenzene with haloalkoxide salt, that is, obtained by reacting alcohol substituted with halogen with appropriate base. Alcohol and base are preferably used about 1–2.5 equivalents to the 2-chloronitrobenzene. It is preferable that reaction solvent is selected from dimethylformamide, ether or tetrahydrofuran, and that the base is selected from sodium, sodium hydride or sodium amide, etc. Reaction is preferably maintained at –10–100° C. for 24–72 hours. The reaction is finished at the time of all the 2-chloronitrobenzene being consumed, and it can be easily observed by the TLC.

2) 2-Haloalkoxyaniline compound (II) can be obtained by reduction of compound (XI). The preferred reducing agent is 3–7 equivalents of iron powder to the compound (XI), and the preferred reaction solvent is mixture of acetic acid and methanol or aqueous hydrochloric acid. Preferably, the reaction is maintained at 50–120° C. for 0.5–2 hours. Reaction is finished at the time of all the compound (XI) being consumed, and it can be easily observed by the TLC.

Typical examples of the haloalkoxypyrrolo[3,2-c]quinoline derivatives, as represented by Formula I, according to the present invention are shown in Table I, as follows:

TABLE I

| Number of compound | $R_1$ | $R_2/R_3$ | $R_4$ | A |
|---|---|---|---|---|
| 1 | OCF$_3$ | 2-CH$_3$ | NHCH$_3$ | CH$_2$CH$_2$ |
| 2 | OCF$_3$ | 2-CH$_3$ | NH(CH$_2$)$_2$OH | CH$_2$CH$_2$ |
| 3 | OCF$_3$ | 2-CH$_3$ | NH(CH$_2$)$_3$OH | CH$_2$CH$_2$ |
| 4 | OCF$_3$ | 2-CH$_3$ | NH(CH$_2$)$_4$OH | CH$_2$CH$_2$ |
| 5 | OCF$_3$ | 2-CH$_3$ | NH(CH$_2$)$_5$OH | CH$_2$CH$_2$ |
| 6 | OCF$_3$ | 2-CH$_3$ | NHCH$_2$CH$_3$ | CH$_2$CH$_2$ |
| 7 | OCF$_3$ | 2-CH$_3$ | Cl | CH$_2$CH$_2$ |
| 8 | OCF$_3$ | 2-CH$_3$ | H | CH=CH |

TABLE I-continued

| Number of compound | $R_1$ | $R_2/R_3$ | $R_4$ | A |
|---|---|---|---|---|
| 9 | $OCF_3$ | 2-$CH_3$ | Cl | CH=CH |
| 10 | $OCF_3$ | 2-$CH_3$ | $NHCH_3$ | CH=CH |
| 11 | $OCF_3$ | 2-$CH_3$ | $NH(CH_2)_2OH$ | CH=CH |
| 12 | $OCF_3$ | 2-$CH_3$ | $NH(CH_2)_2OH$ | CH=CH |
| 13 | $OCF_3$ | 2-$CH_3$ | $NH_2$ | CH=CH |
| 14 | $OCF_3$ | 2-$CH_2CH_3$ | $NH(CH_2)_2OH$ | $CH_2CH_2$ |
| 15 | $OCF_3$ | 2-$CH_2CH_3$ | $NH(CH_2)_3OH$ | $CH_2CH_2$ |
| 16 | $OCF_3$ | 2-$OCH_3$ | $NH(CH_2)_2OH$ | $CH_2CH_2$ |
| 17 | $OCF_3$ | 2-$OCH_3$ | $NH(CH_2)_3OH$ | $CH_2CH_2$ |
| 18 | $OCF_3$ | 2-$OCH_3$ | $NHCH_2CH_3$ | $CH_2CH_2$ |
| 19 | $OCF_3$ | 2,3-$(CH_3)_2$ | $NH(CH_2)_2OH$ | $CH_2CH_2$ |
| 20 | $OCF_3$ | 2,3-$(CH_3)_2$ | $NH(CH_2)_3OH$ | $CH_2CH_2$ |
| 21 | $OCF_3$ | 2-$CH_3$/4-F | $NHCH_3$ | $CH_2CH_2$ |
| 22 | $OCF_3$ | 2-$CH_3$/4-F | $NH(CH_2)_2OH$ | $CH_2CH_2$ |
| 23 | $OCF_3$ | 2-$CH_3$/4-F | $NH(CH_2)_3OH$ | $CH_2CH_2$ |
| 24 | $OCF_3$ | 2-$CH_3$/4-F | $NH(CH_2)_4OH$ | $CH_2CH_2$ |
| 25 | $OCF_3$ | 2-$CH_3$/4-F | $NHCH_3$ | CH=CH |
| 26 | $OCF_3$ | 2-$CH_3$/4-F | $NH(CH_2)_2OH$ | CH=CH |
| 27 | $OCF_3$ | 2-$CH_3$/4-F | $NH(CH_2)_3OH$ | CH=CH |
| 28 | $OCF_3$ | 2-$CH_3$/4-$OCH_3$ | $NH(CH_2)_2OH$ | $CH_2CH_2$ |
| 29 | $OCF_3$ | 2-$CH_3$/4-$OCH_3$ | $NH(CH_2)_3OH$ | $CH_2CH_2$ |
| 30 | $OCF_3$ | 2-$CH_3$/4-OH | $NHCH_3$ | $CH_2CH_2$ |
| 31 | $OCF_3$ | 2-$CH_3$/4-OH | $NH(CH_2)_2OH$ | $CH_2CH_2$ |
| 32 | $OCF_3$ | 2-$CH_3$/4-OH | $NH(CH_2)_3OH$ | $CH_2CH_2$ |
| 33 | $OCF_3$ | 2-$CH_3$/4-OH | $NH(CH_2)_2OH$ | CH=CH |
| 34 | $OCF_3$ | 2-$CH_3$/4-OH | $NH(CH_2)_2OH$ | CH=CH |
| 35 | $OCH_2CF_3$ | 2-$CH_3$ | $NHCH_3$ | $CH_2CH_2$ |
| 36 | $OCH_2CF_3$ | 2-$CH_3$ | $NH(CH_2)_2OH$ | $CH_2CH_2$ |
| 37 | $OCH_2CF_3$ | 2-$CH_3$ | $NH(CH_2)_3OH$ | $CH_2CH_2$ |
| 38 | $OCH_2CF_3$ | 2-$CH_3$ | $NH(CH_2)_4OH$ | $CH_2CH_2$ |
| 39 | $OCH_2CF_3$ | 2-$CH_3$ | $NHCH_3$ | CH=CH |
| 40 | $OCH_2CF_3$ | 2-$CH_3$ | $NH(CH_2)_2OH$ | CH=CH |
| 41 | $OCH_2CF_3$ | 2-$CH_3$ | $NH(CH_2)_3OH$ | CH=CH |
| 42 | $OCH_2CF_3$ | 2-$CH_3$ | $NH(CH_2)_4OH$ | CH=CH |
| 43 | $OCH_2CF_3$ | 2-$OCH_3$ | $NHCH_3$ | $CH_2CH_2$ |
| 44 | $OCH_2CF_3$ | 2-$OCH_3$ | $NH(CH_2)_2OH$ | $CH_2CH_2$ |
| 45 | $OCH_2CF_3$ | 2-$OCH_3$ | $NH(CH_2)_3OH$ | $CH_2CH_2$ |
| 46 | $OCH_2CF_3$ | 2-$OCH_3$ | $NH(CH_2)_4OH$ | $CH_2CH_2$ |
| 47 | $OCH_2CF_3$ | 2-$CH_3$/4-F | $NHCH_3$ | $CH_2CH_2$ |
| 48 | $OCH_2CF_3$ | 2-$CH_3$/4-F | $NH(CH_2)_2OH$ | $CH_2CH_2$ |
| 49 | $OCH_2CF_3$ | 2-$CH_3$/4-F | $NH(CH_2)_3OH$ | $CH_2CH_2$ |
| 50 | $OCH_2CF_3$ | 2-$CH_3$/4-F | $NH(CH_2)_4OH$ | $CH_2CH_2$ |
| 51 | $OCH_2CF_3$ | 2-$CH_3$/4-F | $NHCH_3$ | CH=CH |
| 52 | $OCH_2CF_3$ | 2-$CH_3$/4-F | $NH(CH_2)_2OH$ | CH=CH |
| 53 | $OCH_2CF_3$ | 2-$CH_3$/4-$PhCH_2O$ | $NH(CH_2)_2OH$ | $CH_2CH_2$ |
| 54 | $OCH_2CF_3$ | 2-$CH_3$/4-$OCH_3$ | $NHCH_3$ | $CH_2CH_2$ |
| 55 | $OCH_2CF_3$ | 2-$CH_3$/4-$OCH_3$ | $NH(CH_2)_2OH$ | $CH_2CH_2$ |
| 56 | $OCH_2CF_3$ | 2-$CH_3$/4-$OCH_3$ | $NH(CH_2)_3OH$ | $CH_2CH_2$ |
| 57 | $OCH_2CF_3$ | 2-$CH_3$/4-$OCH_3$ | $NHCH_3$ | CH=CH |
| 58 | $OCH_2CF_3$ | 2-$CH_3$/4-OH | $NHCH_3$ | $CH_2CH_2$ |
| 59 | $OCH_2CH_3$ | 2-$CH_3$/4-OH | $NH(CH_2)_2OH$ | $CH_2CH_2$ |
| 60 | $OCH_2CF_3$ | 2-$CH_3$/4-OH | $NH(CH_2)_3OH$ | CH=CH |
| 61 | $OCH_2CF_3$ | 2-$CH_3$/4-OH | $NH(CH_2)_3OH$ | CH=CH |
| 62 | $OCH_2CF_2CF_3$ | 2-$CH_3$ | $NH(CH_2)_2OH$ | $CH_2CH_2$ |
| 63 | $OCH_2CF_2CF_3$ | 2-$CH_3$ | $NH(CH_2)_3OH$ | $CH_2CH_2$ |
| 64 | $OCH_2CF_2CF_3$ | 2-$CH_3$ | $NH(CH_2)_2OH$ | CH=CH |
| 65 | $OCH_2CF_2CF_3$ | 2-$CH_3$ | $NH(CH_2)_3OH$ | CH=CH |
| 66 | $OCH_2CF_2CF_3$ | 2-$CH_3$/4-$OCH_3$ | $NH(CH_2)_2OH$ | $CH_2CH_2$ |
| 67 | $OCH_2CF_2CF_3$ | 2-$CH_3$/4-$OCH_3$ | $NH(CH_2)_2OH$ | CH=CH |
| 68 | $OCHF_2$ | 2-$CH_3$ | $NHCH_3$ | $CH_2CH_2$ |
| 69 | $OCHF_2$ | 2-$CH_3$ | $NH(CH_2)_2OH$ | CH=CH |
| 70 | $OCHF_2$ | 2-$CH_3$/4-$OCH_3$ | $NH(CH_2)_2OH$ | $CH_2CH_2$ |
| 71 | $OCHF_2$ | 2-$CH_3$/4-$OCH_3$ | $NH(CH_2)_3OH$ | CH=CH |
| 72 | $OCHF_2$ | 2-$CH_3$/4-F | $NH(CH_2)_2OH$ | $CH_2CH_2$ |
| 73 | $OCHF_2$ | 2-$CH_3$/4-F | $NH(CH_2)_3OH$ | CH=CH |
| 74 | $OCHF_2$ | 2-$CH_3$/4-OH | $NHCH_3$ | $CH_2CH_2$ |
| 75 | $OCH_2CH_2F$ | 2-$CH_3$ | $NHCH_3$ | $CH_2CH_2$ |
| 76 | $OCH_2CH_2F$ | 2-$CH_3$ | $NH(CH_2)_2OH$ | CH=CH |
| 77 | $OCH_2CH_2F$ | 2-$CH_3$/4-$OCH_3$ | $NH(CH_2)_2OH$ | $CH_2CH_2$ |
| 78 | $OCH_2CH_2F$ | 2-$CH_3$/4-$OCH_3$ | $NH(CH_2)_3OH$ | $CH_2CH_2$ |
| 79 | $OCH_2CH2F$ | 2-$CH_3$/4-F | $NH(CH_2)_2OH$ | $CH_2CH_2$ |
| 80 | $OCH_2CH_2F$ | 2-$CH_3$/4-OH | $NH(CH_2)_2OH$ | CH=CH |

While the invention has been described by reference to specific examples chosen for the purposes of illustration, it should be apparent that the present invention be not limited by the specific disclosure herein and numerous modifications could be made thereto by those skilled in the art without departing from the basic concept and scope of the invention.

EXAMPLES

Example 1

Preparation of 1-(2-methylphenyl)-4-methylamino-6-trifluoromethoxy-2,3-dihydropyrrolo[3,2-c]quinoline (Step 1) Preparation of diethyl 2-(ethoxyethyl)malonate Sodium(3.4 g, 150 mmol) was added in ethanol(100 ml) at 0°, then stirred at room temperature until the sodium was disappeared. To this mixture was slowly added diethylmalonate(27 ml, 180 mmol), and stirred for 15 minutes at 40°. Hereto was slowly added 2-bromoethyl ether(11.2 ml, 100 mmol) for 30 minutes at room temperature, then the resultant solution was refluxed for 4 hours, cooled and concentrated. The residue was dissolved in n-hexane(200 ml) and washed with brine. The organic layer was fractionally distilled to obtain 22 g of desired compound as liquid in 98% of yield.

b.p 120–127° C./2 mm Hg; $^1$H NMR(CDCl$_3$, 200 MHz) δ 1.01–1.39(m, 9H), 2.02–2.22(m, 2H), 3.25–3.53(m, 5H), 4.01–4.27(m, 4H); m/e 233(M$^+$).

(Step 2) Preparation of 4-oxo-6-trifluoromethoxy-2,3,4,5-tetrahydrofuro[3,2-c]quinoline 2-Trifluoromethoxy aniline(5.10 g, 30 mmol) was dissolved in diphenyl ether(50 ml), and diethyl 2-(ethoxyethyl)malonate(7.4 g, 32 mmol) was added. The reaction mixture was stirred at 220° C. for 7 hours, warmed up to 270° C. and refluxed in Dean-Stark apparatus for 24 hours. Reaction solvent, diphenyl ether, was removed from the above mixture by evaporating in vacuo, then the residue was crystallized in dichloromethane/hexane to obtain 2.4 g of desired compound as solid in 35% of yield.

$^1$H NMR(CDCl$_3$, 200 MHz) δ 3.25(t, J=9.3 Hz, 2H), 4.86(t, J=9.3 Hz, 2H), 7.13–7.25(m, 1H), 7.39–7.45(m, 1H), 7.61(dd, J$_1$=8.0, J$_2$=1.3 Hz, 1H), 9.18(brs, 1H); m/e 271 (M$^+$).

(Step 3) Preparation of 1-(2-methylphenyl)-4-oxo-6-trifluoromethoxy-2,3,4,5-tetrahydropyrrolo[3,2-c]quinoline 4-Oxo-6-trifluoromethoxy-2,3,4,5-tetrahydrofuro[3,2-c]quinoline(272 mg, 1.0 mmol) was dissolved in diethylene glycol (10 ml), and 2-methyl aniline(267 µl, 2.5 mmol) was added under nitrogen atmosphere. The reaction mixture was refluxed at 250° C. for 15 hours. The reaction mixture diluted in brine(20 ml), then aqueous layer was extracted with dichloromethane(15 ml) for 3 times. The organic layer was washed with water(15 ml) for 3 times, then dried over anhydrous magnesium sulfate, filtered and concentrated under reduced pressure. The residue was purified by silica gel chromatography with ethyl acetate as eluent to obtain 298 mg of desired compound as solid in 83% of yield.

m.p 153–156° C.; $^1$H NMR(CDCl$_3$, 200 MHz) δ 2.31(s, 3H), 3.10–3.37(m, 2H), 3.79(q, J=10.2 Hz, 1H), 4.07–4.21 (m, 1H), 6.58(d, J=8.1 Hz, 1H), 6.73(t, J=8.3 Hz, 1H), 7.09–7.39(m, 5H), 8.71(brs, 1H); m/e 361(M$^+$).

(Step 4) Preparation of 1-(2-methylphenyl)-4-chloro-6-trifluoromethoxy-2,3-dihydropyrrolo[3,2-c]quinoline 1-(2-Methylphenyl)-4-oxo-6-trifluoromethoxy-2,3,4,5-tetrahydropyrrolo[3,2-c]quinoline(1.1 g, 3.1 mmol) was dissolved in phosphoryl chloride(10 ml), then the reaction mixture was refluxed for 2 hours, and cooled. After removing the excess phosphoryl chloride by simple distillation, the residue was added in iced water, neutralized with aqueous sodium hydroxide solution(1N), stirred for 30 minutes at room temperature, and extracted with dichloromethane(20 ml) for 3 times. The organic layer was washed with water(15 ml) for 3 times, dried over anhydrous magnesium sulfate, filtered and concentrated under reduced pressure. The residue was purified by silica gel chromatography to obtain 881 mg of desired compound as solid in 75% of yield.

m.p 150–152° C.; $^1$H NMR(CDCl$_3$, 200 MHz) δ 2.27(s, 3H), 3.32–3.44(m, 2H), 3.88–4.03(m, 1H), 4.11–4.25(m, 1H), 6.73(dd, J$_1$=8.7, J$_2$=1.4 Hz, 1H), 6.81(t, J=7.7 Hz, 1H), 7.16–7.30(m, 5H); m/e 379(M$^+$).

(Step 5) Preparation of 1-(2-methylphenyl)-4-methylamino-6-trifluoromethoxy-2,3-dihydropyrrolo[3,2-c]quinoline 1-(2-Methylphenyl)-4-chloro-6-trifluoromethoxy-2,3-dihydropyrrolo[3,2-c]quinoline(300 mg, 0.79 mmol) was dissolved in ethanol(1.0 ml) and aqueous solution of methylamine(40%, 5 ml) was added. The reaction mixture was refluxed in the pressure tube at 170° C. for 20 hours, and the solvent was removed by distillation under low pressure. The residue was diluted in dichloromethane(20 ml), washed with water(15 ml) for 3 times, dried over anhydrous magnesium sulfate, filtered and concentrated under reduced pressure. The residue was purified by silica gel chromatography to obtain 240 mg of desired compound as solid in 81% of yield.

m.p 134–136° C.; $^1$H NMR(CDCl$_3$, 200 MHz) δ 2.33(s, 3H), 2.91–3.21(m, 2H), 3.18(d, J=4.9 Hz, 3H), 4.05–4.35(m, 3H), 6.62–6.72(m, 2H), 6.99–7.39(m, 5H); m/e 374(M$^+$).

Example 2

Preparation of 1-(2-methylphenyl)-4-[(2-hydroxyethyl)amino]-6-trifluoromethoxy-2,3-dihydropyrrolo[3,2-c]quinoline 1-(2-Methylphenyl)-4-chloro-6-trifluoromethoxy-2,3-dihydropyrrolo[3,2-c]quinoline(380 mg, 1.0 mmol) was dissolved in ethanolamine(5 ml), then reacted at the same condition of Step 5 in the Example 1 to obtain 311 mg of desired compound as solid in 77% of yield.

m.p 155–158° C.; $^1$H NMR(CDCl$_3$, 200 MHz) δ 2.30(s, 3H), 2.91–3.22(m, 2H), 3.58–4.01(m, 5H), 4.05–4.25(m, 1H), 5.01(brs, 1H), 6.65–7.45(m, 8H); m/e 404(M$^+$).

Example 3

Preparation of 1-(2-methylphenyl)-4-[(3-hydroxypropyl)amino]-6-trifluoromethoxy-2,3-dihydropyrrolo[3,2-c]quinoline 1-(2-Methylphenyl)-4-chloro-6-trifluoromethoxy-2,3-dihydropyrrolo[3,2-c]quinoline(380 mg, 1.0 mmol) was dissolved in 3-amino-1-propanol(5 ml), then reacted at the same condition of Step 5 in the Example 1 to obtain 313 mg of desired compound as solid in 75% of yield.

m.p 153–154° C.; $^1$H NMR(CDCl$_3$, 200 MHz) δ 1.07–1.82(m, 2H), 2.28(s, 3H), 2.90–3.25(m, 2H), 3.51–4.00(m, 5H), 4.08–4.25(m, 1H), 5.05(brs, 1H), 6.70–7.51(m, 8H); m/e 418(M$^+$).

Example 4

Preparation of 1-(2-methylphenyl)-4-[(4-hydroxybutyl)amino]-6-trifluoromethoxy-2,3-dihydropyrrolo[3,2-c]quinoline 1-(2-Methylphenyl)-4-chloro-6-trifluoromethoxy-2,3-dihydropyrrolo[3,2-c]quinoline(600 mg, 1.6 mmol) was dissolved in diethylene glycol(10 ml) and hereto was added 4-amino-1-butanol(1.0 ml), then reacted at the same condition of Step 5 in the Example 1 to obtain 510 mg of desired compound as solid in 73% of yield.

$^1$H NMR(CDCl$_3$, 200 MHz) δ 1.71–1.88(m, 4H), 2.35(s, 3H), 2.90–3.22(m, 2H), 3.68–3.84(m, 5H), 4.15–4.28(m, 1H), 4.41(brs, 1H), 6.66–7.35(m, 7H); m/e 432(M$^+$).

Example 5

Preparation of 1-(2-methylphenyl)-4-[(5-hydroxypentyl)amino)]-6-trifluoromethoxy-2,3-dihydropyrrolo[3,2-c]quinoline 1-(2-Methylphenyl)-4-chloro-6-trifluoromethoxy-2,3-dihydropyrrolo[3,2-c]quinoline(600 mg, 1.6 mmol) was dissolved in diethylene glycol(10 ml) and hereto was added 5-amino-1-pentanol(206 μl, 1.9 mmol), then reacted at the same condition of Step 5 in the Example 1 to obtain 609 mg of desired compound as solid in 86% of yield.

$^1$H NMR(CDCl$_3$, 200 MHz) δ 1.65–1.82(m, 6H), 2.35(s, 3H), 2.95–3.14(m, 2H), 3.55–3.77(m, 5H), 4.13–4.22(m, 1H), 4.30(brs, 1H), 6.63–7.42(m, 7H); m/e 446(M$^+$).

Example 6

Preparation of 1-(2-methylphenyl)-4-methylamino-6-trifluoromethoxypyrrolo[3,2-c]quinoline (Step 1) Preparation of 1-(2-methylphenyl)-4-oxo-6-trifluoromethoxy-4,5-dihydropyrrolo[3,2-c]quinoline 1-(2-Methylphenyl)-4-oxo-6-trifluoromethoxy-2,3,4,5-tetrahydropyrrolo[3,2-c]quinoline(722 mg, 2 mmol), prepared by the procedures of Step 1 to Step 3 in the Example 1, was dissolved in diphenyl ether(20 ml), hereto added 40 mg of 5%-Pd/C, and refluxed for 4 hours. The reaction mixture was cooled at room temperature, then purified by silica gel chromatography to obtain 610 mg of desired compound as solid in 85% of yield.

$^1$H NMR(CDCl$_3$, 200 MHz) δ 1.90(s, 3H), 6.99–7.10(m, 2H), 7.15–7.30(m, 2H), 7.35–7.65(m, 5H); m/e 359(M$^+$).

(Step 2) Preparation of 1-(2-methylphenyl-4-chloro-6-trifluoromethoxypyrrolo[3,2-c]quinoline 1-(2-Methylphenyl)-4-oxo-6-trifluoromethoxy-4,5-dihydropyrrolo[3,2-c]quinoline(1.44g, 4.0 mmol) was dissolved in phosphoryl chloride(10 ml) and refluxed for 2 hours. After cooling the reaction mixture, the excess phosphoryl chloride was removed by simple distillation and the residue was poured into iced water, neutralized with aqueous solution of sodium hydroxide(1N), then stirred for 30 minutes at room temperature. It was extracted with dichloromethane(20 ml) for 3 times and the organic layer was washed with water(15 ml) for 3 times, dried over anhydrous magnesium sulfate, filtered and concentrated under reduced pressure. The residue was purified by silica gel chromatography to obtain 1.37 g of desired compound as solid in 91% of yield.

m.p 135–138° C.; $^1$H NMR(CDCl$_3$, 200 MHz) δ 1.92(s, 3H), 6.95–7.01(m, 2H), 7.12–7.28(m, 2H), 7.35–7.62(m, 5H); m/e 377(M$^+$).

(Step 3) Preparation of 1-(2-methylphenyl)-4-methylamino-6-trifluoro-methoxy-pyrrolo[3,2-c]quinoline 1-(2-Methyl)-4-chloro-6-trifluoromethoxypyrrolo[3,2-c]quinoline(377 mg, 1.0 mmol) was dissolved in aqueous solution of methylamine(40%, 10 ml) in the pressure tube, and refluxed at 150° C. for 3 hours. After distilling the reaction solvent under reduced pressure, the residue was diluted in dichloromethane(20 ml), and washed with water (15 ml) for 3 times. The organic layer was dried over anhydrous magnesium sulfate and concentrated under reduced pressure. The residue was purified by silica gel chromatography to obtain 286 mg of desired compound as solid in 77% of yield.

$^1$H NMR(CDCl$_3$, 200 MHz) δ 1.91(s, 3H), 3.30(d, J=4.9 Hz, 3H), 4.95–5.12(m, 1H), 6.83(d, J=2.9 Hz, 1H), 6.85–6.92(m, 3H), 7.01(d, J=2.9 Hz, 1H), 7.19–7.55(m, 4H); m/e 372(M$^+$).

Example 7

Preparation of 1-(2-methylphenyl)-4-[(2-hydroxyethyl)amino]-6-trifluoromethoxypyrrolo[3,2-c]quinoline 1-(2-Methylphenyl)-4-chloro-6-trifluoromethoxypyrrolo[3,2-c]quinoline(377 mg, 1.0 mmol) was dissolved in ethanolamine(10 ml) in the pressure tube, then reacted at the same condition of Step 3 in the Example 6 to obtain 289 mg of desired compound as solid in 72% of yield.

m.p 135–138° C.; $^1$H NMR(CDCl$_3$, 200 MHz) δ 1.90(s, 3H), 2.95–3.21(m, 2H), 3.58–3.95(m, 2H), 5.06(brs, 1H), 6.85–7.56(m, 9H); m/e 302(M$^+$).

Example 8

Preparation of 1-(2-methylphenyl)-4-[(3-hydroxypropyl)amino]-6-trifluoromethoxypyrrolo[3,2-c]quinoline 1-(2-Methylphenyl)-4-chloro-6-trifluoromethoxypyrrolo[3,2-c]quinoline(377 mg, 1.0 mmol) was dissolved in 3-amino-1-propanol(10 ml) in the pressure tube, then reacted at the same condition of Step 3 in the Example 6 to obtain 303 mg of desired compound as solid in 73% of yield.

m.p 160–161° C.; $^1$H NMR(CDCl$_3$, 200 MHz) δ 1.05–1.55(m, 2H), 1.95(s, 3H), 2.91–3.20(m, 2H), 3.55–3.89(m, 2H), 5.01(brs, 1H), 6.91–7.55(m, 9H); m/e 416(M$^+$).

Example 9

Preparation of 1-(2-methylphenyl)-4-amino-6-trifluoromethoxy-pyrrolo[3,2-c]quinoline 1-(2-methylphenyl)-4-chloro-6-trifluoromethoxypyrrolo[3,2-c]quinoline(377 mg, 1.0 mmol) was dissolved in aqueous ammonia(10 ml), then reacted at the same condition of Step 3 in the Example 6 to obtain 29 mg of desired compound as solid in 8% of yield.

$^1$H NMR(CDCl$_3$, 200 MHz) δ 1.97(s, 3H), 6.73(d, J=8.2 Hz, 1H), 6.82(t, J=8.2 Hz, 1H), 6.91(d, J=2.2 Hz, 1H), 7.02(d, J=8.0 Hz, 1H) 7.13(d, J=2.2 Hz, 1H), 7.19–7.58(m, 4H); m/e 357(M$^+$, 2.6), 273(100), 257(23), 136(17).

Example 10

Preparation of 1-(2-ethylphenyl)-4-[(2-hydroxyethyl)amino]-6-trifluoromethoxy-2,3-dihydropyrrolo[3,2-c]quinoline (Step 1) Preparation of 1-(2-ethylphenyl)-4-oxo-6-trifluoromethoxy-2,3,4,5-tetrahydropyrrolo[3,2-c]quinoline 4-Oxo-6-trifluoromethoxy-2,3,4,5-tetrahydrofuro[3,2-c]quinoline(7.0 g, 25.8 mmol) was dissolved in diethylene glycol(30 ml) and 2-ethylaniline(6.7 g, 51 mmol) was added under nitrogen. The reaction mixture was refluxed at 250° C. for 15 hours. The reaction mixture was diluted in brine(20 ml), then the aqueous layer was extracted with dichloromethane(15 ml) for 3 times. The organic layer was washed with water(15 ml) for 3 times, dried over anhydrous magnesium sulfate, filtered and concentrated under reduced pressure. The residue was purified by silica gel chromatography with ethyl acetate as eluent to obtain 5.1 g of desired compound as solid in 53% of yield.

m.p 198–202° C.; $^1$H NMR(CDCl$_3$, 200 MHz) δ 1.26(t, J=7.9 Hz, 3H), 2.69–2.81(m, 2H), 3.24–3.33(m, 2H), 3.74–3.85(m, 1H), 4.12–4.21(m, 1H), 6.57–6.80(m, 2H), 7.10–7.44(m, 5H), 8.66(brs, 1H); m/e 375(M$^+$), 374(100), 373(81.7), 333(43.0), 331(21.7).

(Step 2) Preparation of 1-(2-ethylphenyl)-4-chloro-6-trifluoromethoxy-2,3-dihydropyrrolo[3,2-c]quinoline 1-(2-Ethylphenyl)-4-oxo-6-trifluoromethoxy-2,3,4,5-tetrahydropyrrolo[3,2-c]quinoline(2.5 g, 6.7 mmol) was dissolved in phosphoryl chloride(10 ml), then the reaction mixture was refluxed for 2 hours. After removing the excess phosphoryl chloride by simple distillation, the residue was poured into iced water, neutralized with aqueous solution of sodium hydroxide(1N), stirred at room temperature for 30 minutes, and extracted with dichloromethane(20 ml) for 3 times. The organic layer was washed with water(15 ml) for 3 times, dried over anhydrous magnesium sulfate, filtered and concentrated under reduced pressure. The residue was purified by silica gel chromatography to obtain 3.2 g of desired compound as solid in 85% of yield.

m.p 142–145° C.; $^1$H NMR(CDCl$_3$, 200 MHz) δ 1.28(t, J=7.9 Hz, 3H), 2.71–2.82(m, 2H), 3.25–3.36(m, 2H), 3.74–3.85(m, 1H), 4.12–4.21(m, 1H), 6.57–6.80(m, 2H), 7.10–7.44(m, 5H); m/e 394(M$^+$+2, 24.1), 393(M$^+$+1, 23.0), 392(M$^+$, 100), 391(23.1), 342(11.3).

(Step 3) Preparation of 1-(2-ethylphenyl)-4-[(2-hydroxyethyl)amino]-6-trifluoromethoxy-2,3-dihydropyrrolo[3,2-c]quinoline 1-(2-Ethylphenyl)-4-chloro-6-trifluoromethoxy-2,3-dihydropyrrolo[3,2-c]quinoline(801 mg, 2.0 mmol) was dissolved in ethanolamine(10 ml), and the reaction mixture was refluxed at 190° C. for 3 hours. The excess solvent was removed by distillation under reduced pressure, and the residue was diluted in dichloromethane(20 ml), then washed with water(15 ml) for 3 times. The organic layer was dried over anhydrous magnesium sulfate, filtered and concentrated under reduced pressure. The residue was purified by silica gel chromatography to obtain 530 mg of desired compound as solid in 62% of yield.

m.p 127–128° C.; $^1$H NMR(CDCl$_3$, 200 MHz) δ 1.25(t, J=7.9 Hz, 3H), 1.38–1.83(brs, 1H), 2.68–2.75(m, 2H), 3.30–3.13(m, 2H), 3.69–3.90(m, 5H), 4.18–4.21(m, 1H), 4.77–5.92(brs, 1H), 6.62–6.68(m, 2H), 7.01–7.34(m, 5H); m/e 417(M$^+$, 12.1), 373(100), 372(92.9).

Example 11

Preparation of 1-(2-ethylphenyl)-4-[(3-hydroxypropyl)amino]-6-trifluoromethoxy-2,3-dihydropyrrolo[3,2-c]quinoline 1-(2-Ethylphenyl)-4-chloro-6-trifluoromethoxy-2,3-dihydropyrrolo[3,2-c]quinoline(801 mg, 2.0 mmol) was dissolved in 3-amino-1-propanol(10 ml) in the pressure tube, then reacted at the same condition of Step 3 in the Example 10 to obtain 560 mg of desired compound as solid in 62% of yield.

m.p 147–148° C.; $^1$H NMR(CDCl$_3$, 200 MHz) δ 1.30(t, J=7.9 Hz, 3H), 1.58–1.68(brs, 1H), 1.77–1.83(m, 2H), 2.68–2.83(m, 2H), 3.05–3.19(m, 2H), 3.62–3.67(m, 2H), 3.38–3.89(m, 3H), 4.17–4.31(brs, 1H), 6.66–6.71(m, 2H), 7.09–7.39(m, 5H); m/e 413(M$^+$, 13.5), 400(57.9), 386(100), 372(44.2).

Example 12

Preparation of 1-(2-methoxyphenyl)-4-[(2-hydroxyethyl)amino]-6-trifluoromethoxy-2,3-dihydropyrrolo[3,2-c]quinoline (Step 1) Preparation of 1-(2-methoxyphenyl)-4-oxo-6-trifluoromethoxy-2,3,4,5-tetrahydropyrrolo[3,2-c]quinoline 4-Oxo-6-trifluoromethoxy-2,3,4,5-tetrahydrofuro[3,2-c]quinoline(272 mg, 1.0 mmol) was dissolved in diethylene glycol(10 ml), and 2-methoxyaniline(281 μl, 2.5 mmol) was added under nitrogen. The reaction mixture was refluxed at 250° C. for 15 hours. The reaction mixture was diluted in brine(20 ml), and the aqueous layer was extracted with dichloromethane(15 ml) for 3 times. The organic layer was washed with water(15 ml) for 3 times, dried over anhydrous magnesium sulfate, filtered, and concentrated under reduced pressure. The residue was purified by silica gel chromatography with ethyl acetate as eluent to obtain 298 mg of desired compound as solid in 76% of yield.

m.p 171–173° C.; $^1$H NMR(CDCl$_3$, 200 MHz) δ 3.18–3.31(m, 2H), 3.76(s, 3H), 3.75–3.95(m, 1H), 4.05–4.27(m, 1H), 6.75–7.48(m, 7H), 8.83(brs, 1H); m/e 377(M$^+$).

(Step 2) Preparation of 1-(2-methoxyphenyl)-4-chloro-6-trifluoromethoxy-2,3-dihydropyrrolo[3,2-c]quinoline 1-(2-Methoxyphenyl)-4-oxo-6-trifluoromethoxy-2,3,4,5-tetrahydro-pyrrolo[3,2-c]quinoline(3.0 g, 8.0 mmol) was dissolved in phosphoryl chloride(10 ml), then reaction mixture was refluxed for 2 hours. After removing the excess phosphoryl chloride by simple distillation, the residue was poured into iced water, neutralized with aqueous solution of sodium hydroxide(1N), stirred at room temperature for 30 minutes, and extracted with dichloromethane(20 ml) for 3 times. The organic layer was washed with water(15 ml) for 3 times, dried over anhydrous magnesium sulfate, filtered, and concentrated under reduced pressure. The residue was purified by silica gel chromatography to obtain 2.7 g of desired compound as solid in 85% of yield.

m.p 140–141° C.; $^1$H NMR(CDCl$_3$, 200 MHz) δ 3.31–3.41(m, 2H), 3.72(s. 3H), 3.91–4.32(m, 2H), 6.71–7.44(m, 7H); m/e 395(M$^+$+2, 24.1), 394(M$^+$+1, 23.0), 393(M$^+$, 100), 392(23.1).

(Step 3) Preparation of 1-(2-methoxyphenyl)-4-[(2-hydroxyethyl)amino]-6-trifluoromethoxy-2,3-dihydropyrrolo[3,2-c]quinoline 1-(2-methoxyphenyl)-4-chloro-6-trifluoromethoxy-2,3-dihydropyrrolo[3,2-c]quinoline(600 mg, 1.5 mmol) was dissolved in ethanolamine(6 ml) in the pressure tube, then refluxed at 190° C. for 3 hours. The solvent was removed by distillation under reduced pressure, then the residue was diluted in dichloromethane(20 ml), and washed with water (15 ml) for 3 times. The organic layer was dried over anhydrous magnesium sulfate, filtered, and concentrated under reduced pressure. The residue was purified by silica gel chromatography to obtain 520 mg of desired compound as solid in 83% of yield.

m.p 141–142° C.; $^1$H NMR (CDCl$_3$, 200 MHz) δ 3.05–3.13(m, 2H), 3.65–3.82(m, 2H), 3.76(s, 3H), 3.90–3.94(m, 3H), 4.29–4.36(m, 1H), 4.87(brs, 1H), 6.78(d, J=7.6 Hz, 1H), 6.89–6.72(m, 3H), 7.19(dd, J=7.7 Hz, 1.7 Hz, 1H), 7.31–7.38(m, 2H); m/e 420(M$^+$, 21.1), 419(35.2), 374 (100).

Example 13

Preparation of 1-(2-methoxyphenyl)-4-[(3-hydroxypropyl)amino]-6-trifluoromethoxy-2,3-dihydropyrrolo[3,2-c]quinoline 1-(2-Methoxyphenyl)-4-chloro-6-trifluoromethoxy-2,3-dihydropyrrolo[3,2-c]quinoline(600 mg, 1.5 mmol) was dissolved in 3-amino-1-propanol(6 ml) in the pressure tube, and reacted at the same condition of Step 3 in the Example 12 to obtain 570 mg of desired compound as solid in 88% of yield.

m.p 158–159° C.; $^1$H NMR (CDCl$_3$, 200 MHz) δ 1.71–1.84 (m, 2H), 3.02–3.10(m, 2H), 3.63(t, J=3.5 Hz, 2H), 3.77(s, 3H), 3.82–3.90(m, 3H), 4.30–4.34(m, 1H), 4.50(brs, 1H), 6.75(d, J=7.6 Hz, 1H), 6.85–6.92(m, 1H), 7.02(t, J=7.6 Hz, 2H), 7.19(dd, J=7.7 Hz, 1.7 Hz, 1H), 7.28–7.35(m, 2H); m/e 434(M$^+$, 15.4), 403(24.1), 388(100).

Example 14

Preparation of 1-(2,3-dimethylphenyl)-4-[(2-hydroxyethyl)amino]-6-trifluoromethoxy-2,3-dihydropyrrolo[3,2-c]quinoline (Step 1) Preparation of 1-(2,3-dimethylphenyl)-4-oxo-6-trifluoromethoxy-2,3,4,5-tetrahydropyrrolo[3,2-c]quinoline 4-Oxo-6-trifluoromethoxy-2,3,4,5-tetrahydrofuro[3,2-c]quinoline(5.0 g, 19 mmol) was dissolved in diethylene glycol(30 ml), and 2,3-dimethylaniline(5.6 ml, 46 mmol) was added under nitrogen. The reaction mixture was refluxed at 250° C. for 15 hours. The reaction mixture was diluted in brine(20 ml), and the aqueous layer was extracted with dichloromethane(15 ml) for 3 times. The organic layer was washed with water(15 ml) for 3 times, dried with by anhydrous magnesium sulfate, filtered, and concentrated under reduced pressure. The residue was purified by silica gel chromatography with ethyl acetate as eluent to obtain 4.5 g of desired compound as solid in 65% of yield.

$^1$H NMR(CDCl$_3$, 200 MHz) δ 2.27(s, 3H), 2.38(s, 3H), 3.09–3.40(m, 2H), 3.79(dq, J$_1$=1.1 Hz, J$_2$=6 Hz, 1H), 4.12–4.20(m, 1H), 6.62(d, J=8.4 Hz, 1H), 6.68–6.78(m. 3H), 7.05–7.32(m, 3H); m/e 375(M$^+$+1, 26.5), 374(M$^+$, 100), 373(76.1), 333(43.0).

(Step 2) Preparation of 1-(2,3-dimethylphenyl)-4-chloro-6-trifluoromethoxy-2,3-dihydropyrrolo[3,2-c]quinoline 1-(2,3-Dimethylphenyl)-4-oxo-6-trifluoromethoxy-2,3,4,5-tetrahydro-pyrrolo[3,2-c]quinoline(4.4 g, 11.8 mmol) was dissolved in phosphoryl chloride(10 ml). The reaction mixture was refluxed for 2 hours. After removing the excess phosphoryl chloride by simple distillation, the residue was poured into iced water, neutralized with aqueous solution of sodium hydroxide(1N), and stirred for 30 minutes. The resultant was extracted with dichloromethane(20 ml) for 3 times, and the organic layer was washed with water(15 ml) for 3 times, dried over anhydrous magnesium sulfate, filtered, and concentrated under reduced pressure. The residue was purified by silica gel chromatography to obtain 4.0 g of desired compound as solid in 87% of yield.

$^1$H NMR (CDCl$_3$, 200 MHz) δ 2.22(s, 3H), 2.39(s, 3H), 3.36–3.44(m, 2H), 3.95(dq, J$_1$=10 Hz, J$_2$=9.6 Hz, 1H), 4.13–4.21(m, 1H), 6.78(d, J=4 Hz, 1H), 6.91–6.99(m, 1H), 7.07(d, J=0.4 Hz, 1H), 7.14–7.30(m, 2H), 7.41(d, J=6 Hz, 1H); m/e 392(M$^+$+2, 20.6), 392(M$^+$, 86.7), 391(27.8), 69(100).

(Step 3) Preparation of 1-(2,3-dimethylphenyl)-4-[(2-hydroxyethyl)amino]-6-trifluoromethoxy-2,3-dihydropyrrolo[3,2-c]quinoline 1-(2,3-Dimethylphenyl)-4-chloro-6-trifluoromethoxy-2,3-dihydropyrrolo[3,2-c]quinoline(500 mg, 1.3 mmol) was dissolved in ethanolamine(6 ml) in the pressure tube, then refluxed at 190° C. for 3 hours. The solvent was removed by distillation under reduced pressure, then the concentrate was diluted in dichloromethane(20 ml), and washed with water (15 ml) for 3 times. The organic layer was dried over anhydrous magnesium sulfate, filtered, and concentrated under reduced pressure. The residue was purified by silica gel chromatography to obtain 380 mg of desired compound as solid in 72% of yield.

$^1$H NMR(CDCl$_3$, 200 MHz) δ 2.27(s, 3H), 2.38(s, 3H), 2.91–3.27(m, 2H), 3.69–3.85(m, 3H), 3.85–3.97(m, 2H), 4.15–4.22(m, 1H), 4.88(brs, 1H), 6.64–6.76(m, 2H), 6.97(d, J=6.2 Hz, 1H), 7.02–7.23(m, 2H), 7.23–7.35(m, 1H); m/e 418(M$^+$, 9.1), 400(7.7), 386(39.8), 372(100).

Example 15

Preparation of 1-(2,3-dimethylphenyl)-4-[(3-hydroxypropyl)amino]-6-trifluoromethoxy-2,3-dihydropyrrolo[3,2-c]quinoline 1-(2,3-Dimethylphenyl)-4-chloro-6-trifluoromethoxy-2,3-dihydropyrrolo[3,2-c]quinoline(500 mg, 1.3 mmol) was dissolved in 3-amino-1-propanol(6 ml) in the pressure tube, then reacted at the same condition of Step 3 in the Example 14 to obtain 300 mg of desired compound as solid in 56% of yield.

m.p 174–178° C.; $^1$H NMR(CDCl$_3$, 200 MHz) δ 1.73–2.10(m, 2H), 2.26(s, 3H), 2.36(s, 3H), 3.05–3.11(m, 2H), 3.62(q, J=5.3 Hz, 2H), 3.73–3.79(m, 2H), 3.82–3.89(m, 2H), 4.15–4.23(m, 1H), 4.49(brs, 1H), 6.69(d, J=4.2 Hz, 2H), 6.93(d, J=1.1 Hz, 1H), 7.03–7.18(m, 2H), 7.21–7.25(m, 1H); m/e 431(M$^+$, 16.6), 400(54.6), 386(100), 373(36.8).

Example 16

Preparation of 1-(2-methyl-4-fluorophenyl)-4-methylamino-6-trifluoromethoxy-2,3-dihydropyrrolo[3,2-c]quinoline (Step 1) Preparation of 1-(2-methyl-4-fluorophenyl)-4-oxo-6-trifluoromethoxy-2,3,4,5-tetrahydropyrrolo[3,2-c]quinoline 4-Oxo-6-trifluoromethoxy-2,3,4,5-tetrahydrofuro[3,2-c]quinoline(789 mg, 2.9 mmol) was dissolved in diethylene glycol(30 ml) and 2-methyl-4-fluoroaniline(0.8 ml, 7.3 mmol) was added under nitrogen. The reaction mixture was refluxed at 250° C. for 15 hours. The reaction mixture was diluted in brine(20 ml), and the aqueous solution was extracted with dichloromethane(15 ml) for 3 times. The organic layer was washed with water(15 ml) for 3 times, dried over anhydrous magnesium sulfate, filtered, and concentrated under reduced pressure. The residue was purified by silica gel chromatography with ethyl acetate as eluent to obtain 900 mg of desired compound as solid in 82% of yield.

m.p 258–260° C.; $^1$H NMR(CDCl$_3$, 200 MHz) δ 2.32(s, 3H), 3.15–3.31(m, 2H), 3.72–3.85(m, 1H), 4.05–4.21(m, 1H), 6.55–7.41(m, 6H), 8.65(brs, 1H).

(Step 2) Preparation of 1-(2-methyl-4-fluorophenyl)-4-chloro-6-trifluoromethoxy-2,3-dihydropyrrolo[3,2-c]quinoline 1-(2-Methyl-4-fluorophenyl)-4-oxo-6-trifluoromethoxy-2,3,4,5-tetra-hydropyrrolo[3,2-c]quinoline(620 mg, 1.6 mmol) was dissolved in phosphoryl chloride(10 ml) and the reaction mixture was refluxed for 2 hours. After removing the excess phosphoryl chloride by simple distillation, the residue was poured into iced water, neutralized with aqueous solution of sodium hydroxide(1N), stirred at room temperature for 30 minutes, and extracted with dichloromethane(20 ml) for 3 times. The organic layer was washed with water(15 ml), dried over anhydrous magnesium sulfate, filtered, and concentrated under reduced pressure. The residue was purified by silica gel chromatography with ethyl acetate as eluent to obtain 480 mg of desired compound as solid in 76% of yield.

m.p 132° C.; $^1$H NMR(CDCl$_3$, 200 MHz) δ 2.31(s, 3H), 3.30–3.45(m, 2H), 3.85–4.01(m, 1H), 4.11–4.21(m, 1H), 6.71–7.43(m, 6H).

(Step 3) Preparation of 1-(2-methyl-4-fluorophenyl)-4-methylamino-6-trifluoromethoxy-2,3-dihydropyrrolo[3,2-c]quinoline 1-(2-Methyl-4-fluorophenyl)-4-chloro-6-trifluoromethoxy-2,3-dihydropyrrolo[3,2-c]quinoline(500 mg, 1.3 mmol) was dissolved in aqueous solution of methylamine(40%, 10 ml) in the pressure tube, and the reaction mixture was refluxed at 190° C. for 3 hours. The solvent was removed by distillation under reduced pressure, and the residue was diluted in dichloromethane(20 ml), then washed with water(15 ml) for 3 times. The organic layer was dried over anhydrous magnesium sulfate, filtered, and concentrated under reduced pressure. The residue was purified by silica gel chromatography with ethyl acetate as eluent to obtain 380 mg of desired compound as solid in 72% of yield.

m.p 138–140° C.; $^1$H NMR(CDCl$_3$, 200 MHz) δ 2.3(s, 3H), 2.98–3.24(m, 2H), 3.15–3.21(d, 3H), 3.62–3.81(m, 1H), 4.11–4.20(m, 1H), 6.65–7.31(m, 6H).

Example 17

Preparation of 1-(2-methyl-4-fluorophenyl)-4-[(2-hydroxyethyl)amino]-6-trifluoromethoxy-2,3-dihydropyrrolo[3,2-c]quinoline 1-(2-Methyl-4-fluorophenyl)-4-chloro-6-trifluomethoxy-2,3-dihydropyrrolo[3,2-c]quinoline(500 mg, 1.3 mmol) was dissolved in ethanolamine(10 ml) in the pressure tube, then reacted at the same condition of Step 3 in the Example 16 to obtain 465 mg of desired compound as solid in 93% of yield.

m.p 150–153° C.; $^1$H NMR(CDCl$_3$, 200 MHz) δ 2.35(s, 3H), 3.15–3.21 (m, 2H), 3.71–4.01(m, 1H), 4.15–4.32(m, 5H), 4.85(brs, 1H), 6.65–7.35(m, 6H).

Example 18

Preparation of 1-(2-methyl-4-fluorophenyl)-4-[(3-hydroxypropyl)amino]-6-trifluoromethoxy-2,3-dihydropyrrolo[3,2-c]quinoline 1-(2-Methyl-4-fluorophenyl)-4-chloro-6-trifluoromethoxy-2,3-dihydropyrrolo[3,2-c]quinoline(500 mg, 1.3 mmol) was dissolved in 3-amino-1-propanol(10 ml) in the pressure tube, then reacted at the same condition of Step 3 in the Example 16 to obtain 485 mg of desired compound as solid in 95% of yield.

m.p 135° C.; $^1$H NMR(CDCl$_3$, 200 MHz) δ 1.75–1.85(m, 2H), 2.35(s, 3H), 3.01–3.22(m, 2H), 3.61–3.91(m, 1H), 4.10–4.25(m, 5H), 4.50(brs, 1H), 6.61–7.23(m, 6H).

Example 19

Preparation of 1-(2-methyl-4-fluorophenyl)-4-[(4-hydroxybutyl)amino]-6-trifluoromethoxy-2,3-dihydropyrrolo[3,2-c]quinoline 1-(2-methyl-4-fluorophenyl)-4-chloro-6-trifluoromethoxy-2,3-dihydro-pyrrolo[3,2-c]quinoline(500 mg, 1.3 mmol) was dissolved in 4-amino-1-butanol(5 ml) in the pressure tube, then reacted at the same condition of Step 3 in the Example 16 to obtain 390 mg of desired compound as solid in 74% of yield.

m.p 95° C.; $^1$H NMR(CDCl$_3$, 200 MHz) δ 1.71–1.85(m, 4H), 2.32 (s, 3H), 2.91–3.23(m, 2H), 3.61–3.82(m, 1H), 4.11–4.21(m, 5H), 4.51(brs, 1H), 6.12–7.25(m, 6H).

Example 20

Preparation of 1-(2-methyl-4-fluorophenyl)-4-methylamino-6-trifluoromethoxypyrrolo[3,2-c] quinoline (Step 1) Preparation of 1-(2-methyl-4-fluorophenyl)-4-oxo-6-trifluoro-methoxy-4,5-dihydropyrrolo[3,2-c]quinoline 1-(2-Methyl-4-fluorophenyl)-4-oxo-6-trifluoromethoxy-2,3,4,5-tetrahydropyrrolo[3,2-c]quinoline(1.95 g, 5.7 mmol) was dissolved in diphenyl ether(20 ml) and 5%-Pd/C(40 mg) was added, then the reaction mixture was refluxed for 4 hours. The reaction mixture was cooled at room temperature, and purified by silica gel chromatography to obtain 1.9 g of desired compound as solid in 99% of yield.

m.p 240–245° C.; $^1$H NMR(CDCl$_3$, 200 MHz) δ 2.01(s, 3H), 6.95–6.96(d, J=3.1 Hz, 1H), 7.10–7.11(d, J=3.0 Hz, 1H), 6.63–7.43(m, 6H).

(Step 2) Preparation of 1-(2-methyl-4-fluorophenyl)-4-chloro-6-trifluoro-methoxypyrrolo[3,2-c]quinoline 1-(2-Methyl-4-fluorophenyl)-4-oxo-6-trifluoromethoxy-4,5-dihydropyrrolo[3,2-c]quinoline(1.4 g, 4.0 mmol) was dissolved in phosphoryl chloride(10 ml). The reaction mixture was refluxed for 2 hours. After removing the excess phosphoryl chloride by simple distillation, the residue was poured into iced water, neutralized with aqueous solution of sodium hydroxide(1N), and stirred at room temperature for 30 minutes. The reaction mixture was extracted with dichloromethane(20 ml) for 3 times, and the organic layer was washed with water(15 ml) for 3 times, neutralized with anhydrous magnesium sulfate, filtered, and concentrated under reduced pressure. The residue was purified by silica gel chromatography to obtain 1.3 g of desired compound as solid in 89% of yield.

m.p 141° C.; $^1$H NMR(CDCl$_3$, 200 MHz) δ 1.95(s, 3H), 7.01(d, J=3.3 Hz, 1H), 7.18(d, J=3.2 Hz, 1H), 6.98–7.50(m, 6H).

(Step 3) Preparation of 1-(2-methyl-4-fluorophenyl)-4-methylamino-6-trifluoromethoxypyrrolo[3,2-c]quinoline 1-(2-Methyl-4-fluorophenyl)-4-chloro-6-trifluoromethoxy-2,3,4,5-tetrahydropyrrolo[3,2-c]quinoline (394 mg, 1.0 mmol) was dissolved in aqueous solution of methylamine (40%, 10 ml) in the pressure tube. The reaction mixture was refluxed at 180° C. for 3 hours. After removing the reaction solvent of the above mixture, the residue was diluted in dichloromethane(20 ml), and washed with water (15 ml) for 3 times. The organic layer was dried over anhydrous magnesium sulfate, filtered, and concentrated under reduced pressure. The residue was purified by silica gel chromatography to obtain 301 mg of desired compound as solid in 77% of yield.

m.p 150° C.; $^1$H NMR(CDCl$_3$, 200 MHz) δ 1.91(s, 3H), 3.28–3.35(m, 3H), 5.05(brs, 1H), 6.61–7.01(m, 2H), 6.75–7.41(m, 6H).

Example 21

Preparation of 1-(2-methyl-4-fluorophenyl)-4-[(2-hydroxyethyl)amino]-6-trifluoromethoxypyrrolo[3,2-c]quinoline 1-(2-Methyl-4-fluorophenyl)-4-chloro-6-trifluoromethoxypyrrolo[3,2-c]quinoline(394 mg, 1.0 mmol) was dissolved in ethanolamine(5 ml) in the pressure tube, and reacted at the same condition of Step 3 in the Example 20 to obtain 478 mg of desired compound as solid in 90% of yield.

m.p 74–78° C.; $^1$H NMR(CDCl$_3$, 200 MHz) δ 1.9 (s, 3H), 3.81–3.92(m, 2H), 3.95–4.03(m, 2H), 5.60(brs, 1H), 6.67(d, J=3.3 Hz, 1H), 7.01(d, J=3.0 Hz, 1H), 6.75–7.43(m, 6H).

Example 22

Preparation of 1-(2-methyl-4-fluorophenyl)-4-[(3-hydroxy-propyl)amino]-6-trifluoromethoxypyrrolo[3,2-c]quinoline 1-(2-Methyl-4-fluorophenyl)-4-chloro-6-trifluoromethoxypyrrolo[3,2-c]quinoline(394 mg, 1.0 mmol) was dissolved in 3-amino-1-propanol(5 ml) in the pressure tube, and reacted at the same condition of Step 3 in the Example to obtain 460 mg of desired compound as solid in 83% of yield.

m.p 153° C.; $^1$H NMR(CDCl$_3$, 200 MHz) δ 1.81–1.92(m, 2H), 1.95(s, 3H), 3.71–3.82 (m, 2H), 3.90–4.03(m, 2H), 5.15(brs, 1H), 5.75(brs, 1H), 6.65(d, J=3.1 Hz, 1H), 7.05(d, J=3.2 Hz, 1H), 6.73–7.42(m, 6H).

Example 23

Preparation of 1-(2-methyl-4-methoxyphenyl)-4-[(2-hydroxyethyl)amino]-6-trifluoromethoxy-2,3-dihydropyrrolo[3,2-c]quinoline (Step 1) Preparation of 1-(2-methyl-4-methoxyphenyl)-4-oxo-6-trifluoro-methoxy-2,3,4,5-tetrahydropyrrolo[3,2-c]quinoline 4-Oxo-6-trifluoromethoxy-2,3,4,5-tetrahydrofuro[3,2-c]quinoline(5.0 g, 19 mmol) was dissolved in diethylene glycol(30 ml) and 2-methyl-4-methoxyaniline(6.1 ml, 46 mmol) was added. The reaction mixture was refluxed at 250° C. for 15 hours, diluted in brine(20 ml), and the aqueous layer was extracted with dichloromethane(15 ml) for 3 times. The organic layer was washed with water(15 ml) for 3 times, dried over anhydrous magnesium sulfate, filtered, and concentrated under reduced pressure. The residue was purified with ethyl acetate as eluent by silica gel chromatography to obtain 6.6 g of desired compound as solid in 91% of yield.

$^1$H NMR(CDCl$_3$, 200 MHz) δ 2.29(s, 3H), 3.20–3.26(m, 2H), 3.74–3.80(m, 1H), 3.85(s, 3H), 4.10–4.12(m, 1H), 6.52–6.92(m, 4H), 7.10(d, J=8.46 Hz, 1H), 7.28–7.31(m, 1H); m/e 390(M$^+$, 100), 389(80.4), 349(33.5).

(Step 2) Preparation of 1-(2-methyl-4-methoxyphenyl)-4-chloro-6-trifluoromethoxy-2,3-dihydropyrrolo[3,2-c]quinoline 1-(2-Methyl-4-methoxyphenyl)-4-oxo-6-trifluoromethoxy-2,3,4,5-tetrahydropyrrolo[3,2-c]quinoline (4.0 g, 10 mmol) was dissolved in phosphoryl chloride(10 ml). The reaction mixture was refluxed for 2 hours, and cooled. After removing the excess phosphoryl chloride by simple distillation, the residue was poured into iced water, neutralized with aqueous solution of sodium hydroxide (1N), and stirred at room temperature for 30 minutes. It was extracted with dichloromethane(20 ml) for 3 times, and the organic layer was washed with water (15 ml) for 3 times, dried over anhydrous magnesium sulfate, filtered, and concentrated under reduced pressure. The residue was purified by silica gel chromatography to obtain 2.8 g of desired compound as solid in 70% of yield.

$^1$H NMR (CDCl$_3$, 200 MHz) δ 2.25(s, 3H), 3.34–3.38(m, 2H), 3.88(s, 3H), 4.08–4.12(m, 2H), 6.75–7.01(m, 4H), 7.15(d, J=8.42 Hz, 1H), 7.38–7.42(m, 1H); m/e 410($M^+$+2, 72.5), 409($M^+$+1, 37.3), 408($M^+$, 100), 407(32.1).

(Step 3) Preparation of 1-(2-methyl-4-methoxyphenyl)-4-[(2-hydroxyethyl)amino]-6-trifluoromethoxy-2,3-dihydropyrrolo[3,2-c]quinoline 1-(2-Methyl-4-methoxyphenyl)-4-chloro-6-trifluoromethoxy-2,3-dihydropyrrolo[3,2-c]quinoline(550 mg, 1.3 mmol) was dissolved in ethanolamine(10 ml) in the pressure tube. The reaction mixture was refluxed at 190° C. for 3 hours. After removing the reaction solvent under reduced pressure, the residue was diluted in dichloromethane(20 ml), and washed with water(15 ml) for 3 times. The organic layer was dried over anhydrous magnesium sulfate, filtered, and concentrated under reduced pressure. The residue was purified by silica gel chromatography to obtain 510 mg of desired compound as solid in 91% of yield.

m.p 104–105° C.; $^1$H NMR(CDCl$_3$, 200 MHz) δ 2.29(s, 3H), 3.06–3.09(m, 2H), 3.68–3.82(m, 3H), 3.86(s, 3H), 3.90–3.96(m, 2H), 4.13–4.17(m, 1H), 4.88(brs, 1H), 6.67–6.87(m, 4H), 7.08(d, J=9 Hz, 1H), 7.30–7.33(m, 1H); m/e 434($M^+$+1, 6.6), 433($M^+$, 7.4), 403(19.5), 388(100).

Example 24

Preparation of 1-(2-methyl-4-methoxyphenyl)-4-[(3-hydroxypropyl)amino]-6-trifluoromethoxy-2,3-dihydropyrrolo[3,2-c]quinoline 1-(2-Methyl-4-methoxyphenyl)-4-chloro-6-trifluoromethoxy-2,3-dihydropyrrolo[3,2-c]quinoline(550 mg, 1.3 mmol) was dissolved in 3-amino-1-propanol(10 ml) in the pressure tube, and reacted at the same condition of Step 3 in the Example 23 to obtain 400 mg of desired compound as solid in 67% of yield.

m.p 157–159° C.; $^1$H NMR(CDCl$_3$, 200 MHz) δ 1.74–1.78(m, 2H), 2.31(s, 3H), 3.08–3.10(m, 2H), 3.65(q, J=5 Hz, 2H), 3.73–3.92(m, 3H), 3.88(s, 3H), 4.14–4.18 (m, 1H), 4.52(brs, 1H), 6.67–6.78(m, 2H), 6.77–6.81(m, 1H), 6.89(d, J=3.1 Hz, 1H), 7.08(d, J=8.2 Hz, 1H), 7.28–7.32(m, 1H); m/e 447($M^+$, 22.1), 416(60.3), 402(100), 387(15.3).

Example 25

Preparation of 1-(2-methyl-4-hydroxyphenyl)-4-methylamino-6-trifluoromethoxy-2,3-dihydropyrrolo[3,2-c]quinoline (Step 1) Preparation of 1-(2-methyl-4-hydroxyphenyl)-4-oxo-6-trifluoromethoxy-2,3,4,5-tetrahydropyrrolo[3,2-c]quinoline 4-Oxo-6-trifluoromethoxy-2,3,4,5-tetrahydrofuro[3,2-c]quinoline(5.0 g, 19 mmol) was dissolved in ethylene glycol (30 ml) and 4-amino-m-cresol (5.6 g, 46 mmol) was added under nitrogen. The reaction mixture was refluxed at 250° for 15 hours. After diluting the reaction mixture in brine(20 ml), the aqueous layer was extracted with dichloromethane (15 ml) for 3 times. The organic layer was washed with water(15 ml) for 3 times, dried over anhydrous magnesium sulfate, filtered, and concentrated under reduced pressure. The residue was purified with ethyl acetate as eluent by silica gel chromatography to obtain 6.6 g of desired compound as solid in 91% of yield.

$^1$H NMR(CDCl$_3$, 200 MHz) δ 2.27(s, 3H), 3.20–3.28(m, 2H), 3.71–3.80(m, 1H), 4.10–4.15(m, 1H), 6.52–6.85(m, 4H), 7.12(d, J=8.5 Hz, 1H), 7.28–7.34(m, 1H); m/e 376($M^+$, 100), 375(85.4), 335(23.5).

(Step 2) Preparation of 1-(2-methyl-4-methanesulfoxyphenyl)-4-oxo-6-trifluoromethoxy-2,3,4,5-tetrahydropyrrolo[3,2-c]quinoline 1-(2-Methyl-4-hydroxyphenyl)-4-oxo-6-trifluoromethoxy-2,3,4,5-tetra-hydropyrrolo[3,2-c]quinoline(2.3g, 6.1 mmol) was dissolved in dichloromethane. Triethylamine(2.6 ml, 18.0 mmol) was added and methanesulfonyl chloride(1.0 ml, 12.8 mmol) were added, and then the reaction mixture was stirred at −78° C. for 3 hours. The reaction mixture was slowly warmed up to −10° C., and stirred for 1 hours. After extracting the reaction mixture with dichloromethane, the organic layer was washed with water for 3 times. The organic layer was dried over anhydrous magnesium sulfate, filtered, and concentrated under reduced pressure. The residue was crystallized in dichloromethane/hexane to obtain 2.3 g of desired compound as solid in 72% of yield.

m.p 232–235° C.; $^1$H NMR(CDCl$_3$, 200 MHz) δ 2.37(s, 3H), 3.21(s, 3H), 3.07–3.37(m, 2H), 3.72(q, J=11.2 Hz, 1H), 4.06–4.23(m, 1H), 6.59(d, J=8.3 Hz, 1H), 6.71(t, J=8.3 Hz, 1H), 7.12(s, 1H), 7.21–7.35(m, 3H), 8.74(brs, 1H); m/e 455($M^+$, 29.0), 454(51.4), 453(14.0), 376(31.6), 375(100).

(Step 3) Preparation of 1-(2-methyl-4-methanesulfoxyphenyl)-4-chloro-6-trifluoromethoxy-2,3-dihydropyrrolo[3,2-c]quinoline 1-(2-Methyl-4-methanesulfoxyphenyl)-4-oxo-6-trifluoromethoxy-2,3,4,5-tetrahydropyrrolo[3,2-c]quinoline (1.18 g, 2.6 mmol) was dissolved in phosphoryl chloride(15 ml), stirred at 110° C. for 30 minutes. After removing the excess phosphoryl chloride by distillation, the residue was diluted in dichloromethane(20 ml), neutralized with aqueous solution of sodium bicarbonate, and stirred at room temperature for 30 minutes. The resultant was extracted with dichloromethane, and the organic layer was washed with water for 3 times. The organic layer was dried over anhydrous magnesium sulfate, filtered, and concentrated under reduced pressure. The residue was purified by silica gel column chromatography (ethyl acetate:hexane=1:5) to obtain 1.2 g of desired compound as solid in 92% of yield.

m.p 141–143° C.; $^1$H NMR(CDCl$_3$, 200 MHz) δ 2.35(s, 3H), 3.20(s, 3H), 3.27–3.54(m, 2H), 3.91(q, J=10.2 Hz, 1H), 4.11–4.29(m, 1H), 6.77(d, J=8.7 Hz, 1H), 7.01(t, J=8.7 Hz, 1H), 7.12–7.47(m, 4H); m/e 474($M^+$+2, 29.3), 473($M^+$+1, 17.2), 472($M^+$, 57.9), 395(30.8), 394(28.3), 393(100), 349 (16.4).

(Step 4) Preparation of 1-(2-methyl-4-hydroxyphenyl)-4-methylamino-6-trifluoromethoxy-2,3-dihydropyrrolo[3,2-c]quinoline 1-(2-Methyl-4-methanesulfoxyphenyl)-4-chloro-6-trifluoromethoxy-2,3-dihydropyrrolo[3,2-c]quinoline(500 mg, 1.1 mmol) was dissolved in aqueous solution of methylamine(40%, 5.0 ml), and the reaction mixture was refluxed at 180° C. for 15 hours in the pressure tube. The reaction mixture was dissolved in water, extracted with dichloromethane, and the organic layer was washed with water for 3 times. The organic layer was dried over anhydrous magnesium sulfate, filtered, and concentrated under reduced pressure. The residue was purified by silica gel column chromatography(ethyl acetate:hexane=1:1) to obtain 50 mg of desired compound as solid in 85% of yield.

m.p 161–163° C.; $^1$H NMR(CDCl$_3$, 200 MHz) δ 2.22(s, 3H), 2.87–3.15(m, 2H), 3.20(s, 2H), 3.72(q, J=8.2 Hz, 1H), 4.03–4.21(m, 1H), 6.56–6.81(m, 4H), 6.92(d, J=8.1 Hz, 1H), 7.21–7.30(m, 1H); m/e 390($M^+$, 14.4), 389(75.7), 388(100), 372(11.5), 360(9.5).

Example 26

Preparation of 1-(2-methyl-4-hydroxyphenyl)-4-[(2-hydroxyethyl)amino]-6-trifluoromethoxy-2,3-dihydropyrrolo[3,2-c]quinoline 1-(2-Methyl-4-methanesulfoxyphenyl)-4-chloro-6-trifluoromethoxy-2,3-dihydropyrrolo[3,2-c]quinoline(500 mg, 1.1 mmol) was dissolved in ethanolamine(5.0 ml), then reacted at the same condition of Step 4 in the Example 25 to obtain 401 mg of desired compound as solid in 74% of yield.

m.p 207–209° C.; $^1$H NMR(CDCl$_3$/DMSO-d$_6$, 200 MHz) δ 2.19(s, 3H), 2.95–3.18(m, 2H), 3.61–3.75(m, 2H), 3.75(q, J=10.1 Hz, 1H), 3.73–3.92(m, 2H), 4.02–4.18(m, 1H), 5.35 (brs, 1H), 6.58–6.82(m, 4H), 6.91(d, J=8.6 Hz, 1H), 7.17–7.25(m, 1H); m/e 420(M$^+$, 3.9), 418(3.2), 400(9.1), 389(20.1), 388(26.4), 375(100).

Example 27

Preparation of 1-(2-methyl-4-hydroxyphenyl)-4-[(3-hydroxypropyl)amino]-6-trifluoromethoxy-2,3-dihydropyrrolo[3,2-c]quinoline 1-(2-Methyl-4-methanesulfoxyphenyl)-4-chloro-6-trifluoromethoxy-2,3-dihydropyrrolo[3,2-c]quinoline(500 mg, 1.1 mmol) was dissolved in 3-amino-1-propanol(5.0 ml), then reacted at the same condition of Step 4 in the Example 25 to obtain 375 mg of desired compound as solid in 69% of yield.

m.p 185–187° C.; $^1$H NMR(CDCl$_3$, 200 MHz) δ 1.71–1.87(m, 2H), 2.09(s, 3H), 2.91–3.12(m, 2H), 3.51–3.72(m, 2H), 3.71–3.92(m, 3H), 3.98–4.12(m, 1H), 4.52(brs, 1H), 6.51–6.82(m, 5H), 6.82(d, J=8.1 Hz, 1H), 7.13–7.28(m, 1H); m/e 434(M$^+$, 6.8), 433(30.4), 432(27.5), 403(26.7), 402(62.0), 389(71.7), 388(100), 375(39.4), 334 (10.3).

Example 28

Preparation of 1-(2-methyl-4-hydroxyphenyl)-4-methylamino-6-trifluoromethoxypyrrolo[3,2-c]quinoline (Step 1) Preparation of 1-(2-methyl-4-methanesulfoxyphenyl)-4-oxo-6-trifluoromethoxy-4,5-dihydropyrrolo[3,2-c]quinoline 1-(2-Methyl-4-methanesulfoxyphenyl)-4-oxo-6-trifluoromethoxy-2,3,4,5-tetrahydropyrrolo[3,2-c]quinoline (683 mg, 1.5 mmol) was dissolved in diphenyl ether(10 ml), 10%-Pd/C(100 mg) was added, and the reaction mixture was refluxed at 270° C. for 1 hours. The reaction mixture was purified by silica gel column chromatography(ethyl acetate:dichloromethane=1:1) to obtain 250 mg of desired compound as solid in 38% of yield.

m.p 225–227° C.; $^1$H NMR(CDCl$_3$, 200 MHz) δ 2.03 (s, 3H), 3.21(s, 3H), 6.63(d, J=8.3 Hz, 1H), 6.91(t, J=8.3 Hz, 1H), 6.96(d, J=3.2 Hz), 7.13(d, J=3.2 Hz, 1H), 7.26–7.53(m, 4H), 8.87(brs, 1H); m/e 454(M$^+$, 11.1), 453(21.1), 452 (80.3), 373(100), 345(23.8), 305(16.5), 204(12.6).

(Step 2) Preparation of 1-(2-methyl-4-methanesulfoxyphenyl)-4-chloro-6-trifluoromethoxypyrrolo[3,2-c]quinoline 1-(2-Methyl-4-methanesulfoxyphenyl)-4-oxo-6-trifluoromethoxy-4,5-dihydropyrrolo[3,2-c]quinoline(250 mg, 0.55 mmol) was dissolved with phosphoryl chloride(15 ml). The mixture was stirred at 110° C. for 30 minutes. After removing the excess phosphoryl chloride of the above mixture by distillation, the residue was dissolved in dichloromethane(20 ml), neutralized with aqueous solution of sodium bicarbonate, and stirred at room temperature for 30 minutes. The resultant was extracted with dichloromethane, then the organic layer was washed with water for 3 times, dried over anhydrous magnesium sulfate, filtered, and concentrated under reduced pressure. The residue was purified by silica gel column chromatography (ethyl acetate:hexane=1:5) to obtain 250 mg of desired compound as oil in 96% of yield.

$^1$H NMR(CDCl$_3$, 200 MHz) δ 1.99(s, 3H), 3.32(s, 3H), 7.02(d, J=3.2 Hz, 1H), 7.19(d, J=3.2 Hz, 1H), 7.22–7.29(m, 4H), 7.35–7.53(m, 5H); m/e 472(M$^+$+2, 57.2), 471(M$^+$+1, 19.8), 470(M$^+$, 100), 393(49.1), 392(14.9), 391(84.5), 363 (20.7).

(Step 3) Preparation of 1-(2-methyl-4-hydroxyphenyl)-4-methylamino-6-trifluoromethoxypyrrolo[3,2-c]quinoline 1-(2-Methyl-4-methanesulfoxyphenyl)-4-chloro-6-trifluoromethoxy-pyrrolo[3,2-c]quinoline(150 mg, 0.32 mmol) was dissolved in aqueous solution of methylamine (40%, 5.0 ml), and the reaction mixture was refluxed at 180° C. for 15 hours in the pressure tube. The reaction mixture was dissolved in water, extracted with dichloromethane, and the organic layer was washed with water for 3 times. The organic layer was dried over anhydrous magnesium sulfate, filtered, and concentrated under reduced pressure. The residue was purified by silica gel column chromatography(ethyl acetate:hexane=1:1) to obtain 170 mg of desired compound as solid in 86% of yield.

m.p 205–207° C.; $^1$H NMR(CDCl$_3$, 200 MHz) δ 1.81(s, 3H), 3.32(s, 3H), 4.51(brs, 1H), 6.63(d, J=2.9 Hz, 1H), 6.71–6.92(m, 3H), 6.80(s, 1H), 6.98(d, J=2.9 Hz, 1H), 7.17(d, J=8.3 Hz, 1H), 7.22–7.36(m, 1H); m/e 388(M$^+$, 32.3), 387(100), 360(12.7), 359(38.2), 338(13.7), 271(10.6), 229(10.4).

Example 29

Preparation of 1-(2-methyl-4-hydroxyphenyl)-4-[(2-hydroxyethyl)amino]-6-trifluoromethoxypyrrolo[3,2-c]quinoline 1-(2-Methyl-4-methanesulfoxyphenyl)-4-chloro-6-trifluoromethoxypyrrolo[3,2-c]quinoline(150 mg, 0.32 mmol) was dissolved in ethanolamine(5.0 ml), and reacted at the same condition of Step 3 in the Example 28 to obtain 90 mg of desired compound as solid in 67% of yield.

m.p 210–212° C.; $^1$H NMR(CDCl$_3$/DMSO-d$_6$, 200 MHz) δ 1.82(s, 3H), 3.77–3.87(m, 2H), 3.89–4.01(m, 2H), 6.29 (brs, 1H), 6.78(d, J=3.2 Hz, 1H), 6.78–6.95(m, 4H), 6.99(d, J=3.2 Hz, 1H), 7.12(d, J=8.2 Hz, 1H), 7.21–7.32(m, 1H); m/e 418(M$^+$, 1.7), 417(6.5), 398(14.4), 386(22.3), 373(100), 3.58(7.2).

Example 30

Preparation of 1-(2-methylphenyl)-4-methylamino-6-β,β,β-trifluoroethoxy-2,3-dihydropyrrolo[3,2-c]quinoline (Step 1) Preparation of 2-β,β,β-trifluoroethoxynitrobenzene Sodium hydride(60 wt %, 2.8 g, 65 mmol) was put in flask, under nitrogen, then hereto was added purified tetrahydrofuran(150 ml) and slowly introduced 2,2,2-trifluoroethanol(4.4 ml, 60 mmol) at 0° C., then stirred for 10 minutes at 0° C. After addition of 2-chloronitrobenzene(7.9 g, 50 mmol) in dropwise, the reaction mixture stirred at 10° C. for 72 hours. The reaction mixture was dissolved in water, extracted with ether, and the organic layer was washed with water for 3 times. The organic layer was dried over anhydrous magnesium sulfate, filtered, and concentrated under reduced pressure to obtain 11 g of desired compound as solid in 91% of yield.

$^1$H NMR(CDCl$_3$, 200 MHz) δ 4.46–4.54(q, J=8.0 Hz, 2H), 7.09–7.25(m, 2H), 7.53–7.62(m, 1H), 7.85–7.90(m, 1H); m/e 221(M$^+$).

(Step 2) Preparation of 2-β,β,β-trifluoroethoxyaniline

Iron powder(16.5 g, 300 mmol) was added to 5%-aqueous solution of acetic acid(200 ml), and the resultant was stirred at 80° C. for 30 minutes. Hereto was slowly added 2-β,β,β-trifluoroethoxynitrobenzene(13.3 g, 60 mmol) dissolved in acetic acid, and the resultant was stirred at 100° for 30 minutes. The reaction mixture was extracted with ether, neutralized with aqueous solution of sodium hydroxide(1N), and concentrated to obtain 10.7 g of desired compound as solid in 93% of yield.

$^1$H NMR(CDCl$_3$, 200 MHz) δ 3.82(brs, 2H), 4.36(q, J=8.2 Hz, 2H), 6.68–6.95(m, 4H); m/e 191(M$^+$).

(Step 3) Preparation of 4-oxo-6-β,β,β-trifluoroethoxy-2,3,4,5-tetrahydro-furo[3,2-c]quinoline 2-β,β,β-Trifluoroethoxyaniline(64 g, 34 mmol) was dissolved in diphenyl ether(75 ml) and diethyl-2-(ethoxyethyl)malonate( 82 g, 36 mmol) was added at room temperature. The reaction mixture was stirred at 220° C. for 7 hours, and refluxed at 270° C. for 24 hours in Dean-Stark apparatus. After removing diphenyl ether by distillation in vacuo, the residue was recrystallized in methylene chloride/hexane to obtain 54 g of desired compound as solid in 56% of yield.

$^1$H NMR(CDCl$_3$, 200 MHz) δ 3.23(t, J=9.3 Hz, 2H), 4.52(t, J=8.7 Hz, 2H), 4.86(t, J=9.3 Hz, 2H), 7.15–7.24(m, 1H), 7.37–7.48(m, 1H), 7.63(dd, J$_1$=8.0, J$_2$=1.3 Hz, 1H), 9.21(brs, 1H); m/e 285(M$^+$).

(Step 4) Preparation of 1-(2-methylphenyl)-4-oxo-6-β,β,β-trifluoroethoxy-2,3,4,5-tetrahydropyrrolo[3,2-c]quinoline 4-Oxo-6-β,β,β-trifluoroethoxy-2,3,4,5-tetrahydrofuro[3,2-c]quinoline(4.4 g, 15 mmol) was dissolved in diethylene glycol(10 ml) and 2-methylaniline(7 ml, 37 mmol) was added under nitrogen. The reaction mixture was refluxed at 250° C. for 15 hours. After diluting the reaction mixture in brine(20 ml), the aqueous layer was extracted with dichloromethane(15 ml) for 3 times. The organic layer was washed with water(15 ml) for 3 times, dried over anhydrous magnesium sulfate, filtered, and concentrated under reduced pressure. The residue was purified with ethyl acetate as eluent by silica gel chromatography to obtain 4.7 g of desired compound as solid in 82% of yield.

m.p 167–170° C.; $^1$H NMR(CDCl$_3$, 200 MHz) δ 2.35(s, 3H), 3.11–3.42(m, 2H), 3.76–3.92(m, 1H), 4.11–4.25(m, 1H), 4.49(q, J=4.9 Hz, 2H), 6.37–7.41(m, 7H), 8.75(brs, 1H).

(Step 5) Preparation of 1-(2-methylphenyl)-4-chloro-6-β,β,β-trifluoroethoxy-2,3-dihydropyrrolo[3,2-c]quinoline 1-(2-Methylphenyl)-4-oxo-6-β,β,β-trifluoroethoxy-2,3,4,5-tetrahydro-pyrrolo[3,2-c]quinoline(3.8 g, 10 mmol) was dissolved in phosphoryl chloride(15 ml), then the reaction mixture was refluxed for 2 hours. After removing the excess phosphoryl chloride by simple distillation, the residue was poured into the iced water, neutralized with aqueous solution of sodium hydroxide(1N), and stirred at room temperature for 30 minutes. It was extracted with dichloromethane(20 ml) for 3 times, then the organic layer was washed with water(15 ml) for 3 times, dried over anhydrous magnesium sulfate, filtered, and concentrated under reduced pressure. The residue was purified by silica gel chromatography to obtain 3.1 g of desired compound as solid in 78% of yield.

m.p 135° C.; $^1$H NMR(CDCl$_3$, 200 MHz) δ 2.30(s, 3H), 3.35–3.45(m, 2H), 3.92–4.05(m, 1H), 4.12–4.26(m, 1H), 4.76(q, J=8.6 Hz, 2H), 6.56–7.39(m, 7H).

(Step 6) Preparation of 1-(2-methylphenyl)-4-methylamino-6-β,β,β-trifluoroethoxy-2,3-dihydropyrrolo[3,2-c]quinoline 1-(2-Methylphenyl)-4-chloro-6-β,β,β-trifluoroethoxy-2,3-dihydropyrrolo[3,2-c]quinoline(392 mg, 1.0 mmol) was dissolved in aqueous solution of methylamine(40%, 5.0 ml) and the reaction mixture was refluxed at 180° C. for 15 hours in the pressure tube. The reaction mixture was dissolved in water, extracted with dichloromethane, and the organic layer was washed with water for 3 times. The organic layer was dried over anhydrous magnesium sulfate, filtered, and concentrated under reduced pressure. The residue was purified by silica gel column chromatography(ethyl acetate:hexane=1:1) to obtain 290 mg of desired compound as solid in 75% of yield.

m.p 134–135° C.; $^1$H NMR(CDCl$_3$, 200 MHz) δ 2.32(s, 3H), 2.87–3.15(m, 2H), 3.17(brs, 3H), 3.75(q, J=8.7 Hz, 1H), 4.03–4.21(m, 1H), 4.79(dq, J$_1$=3.1, J$_2$=9.8 Hz, 2H), 6.51–6.58(m, 1H), 6.64(t, J=8.3 Hz, 1H), 6.95–7.32(m, 5H); m/e 388(M$^+$, 9.3), 387(42.5), 386(15.4), 346(5.4), 318(100).

Example 31

Preparation of 1-(2-methylphenyl)-4-[(2-hydroxyethyl)amino]-6-β,β,β-trifluoroethoxy-2,3-dihydropyrrolo[3,2-c]quinoline 1-(2-Methylphenyl)-4-chloro-6-β,β,β-trifluoroethoxy-2,3-dihydropyrrolo[3,2-c]quinoline(500 mg, 1.3 mmol) was dissolved in ethanolamine(5.0 ml), and reacted at the same condition of Step 6 in the Example 30 to obtain 489 mg of desired compound as solid in 92% of yield.

m.p 142–144° C.; $^1$H NMR(CDCl$_3$, 200 MHz) δ 2.33(s, 3H), 3.01–3.16(m, 2H), 3.73–3.93(m, 5H), 4.15–4.33(m, 1H), 4.57(q, J=4.2 Hz, 2H), 4.75(brs, 1H), 6.46–7.35(m, 7H); m/e 418 (M$^+$).

Example 32

Preparation of 1-(2-methylphenyl)-4-[(3-hydroxypropyl)amino]-6-β,β,β-trifluoroethoxy-2,3-dihydropyrrolo[3,2-c]quinoline 1-(2-Methylphenyl)-4-chloro-6-β,β,β-trifluoroethoxy-2,3-dihydropyrrolo[3,2-c]quinoline(500 mg, 1.3 mmol) was dissolved in 3-amino-1-propanol(5.0 ml), and reacted at the same condition of Step 6 in the Example 30 to obtain 496 mg of desired compound as solid in 90% of yield.

m.p 145° C.; $^1$H NMR(CDCl$_3$, 200 MHz) δ 1.74–1.80(m, 2H), 2.33(s, 3H), 3.01–3.15(m, 2H), 3.55–3.91(m, 5H), 4.12–4.25(m, 1H), 4.41(brs, 1H), 4.58(q, J=5.9 Hz, 2H), 6.45–7.33 (m, 7H); m/e 432(M$^+$).

Example 33

Preparation of 1-(2-methylphenyl)-4-[(4-hydroxybutyl)amino]-6-β,β,β-trifluoroethoxy-2,3-dihydropyrrolo[3,2-c]quinoline 1-(2-Methylphenyl)-4-chloro-6-β,β,β-trifluoroethoxy-2,3-dihydropyrrolo[3,2-c]quinoline(500 mg, 1.3 mmol) was dissolved in diethylene glycol(10 ml), then hereto was added 4-amino-1-butanol(175 μl, 1.9 mmol), and reacted at the same condition of Step 6 in the Example 30 to obtain 495 mg of desired compound as solid in 87% of yield.

$^1$H NMR(CDCl$_3$, 200 MHz) δ 1.62–1.85(m, 4H), 2.33(s, 3H), 2.93–3.21(m, 2H), 3.62–3.81(m, 5H), 4.11–4.25(m, 2H), 4.78(m, 2H), 6.55–7.31(m, 7H); m/e 446(M$^+$).

Example 34

Preparation of 1-(2-methylphenyl)-4-methylamino-6-β,β,β-trifluoroethoxypyrrolo[3,2-c]quinoline (Step 1) Preparation of 1-(2-methylphenyl)-4-oxo-6-β,β,β-trifluoroethoxy-4,5-dihydropyrrolo[3,2-c]quinoline 1-(2-Methylphenyl)-4-oxo-6-β,β,β-trifluoroethoxy-2,3,4,5-tetrahydropyrrolo[3,2-c]quinoline(1.0 g, 2.7 mmol), prepared by the procedures of Step 1 to Step 4 in the Example 30, was added in diphenyl ether(10 ml) and 5%-Pd/C(340 mg). The reaction mixture was refluxed for 4 hours. The reaction mixture was cooled at room temperature, and purified by silica gel chromatography to obtain 830 mg of desired compound as solid in 85% of yield.

$^1$H NMR (CDCl$_3$, 200 MHz) δ 1.97(s, 3H), 4.51(q, J=7.9 Hz, 2H), 6.36–7.58(m, 9H), 8.98(brs, 1H); m/e 373 (M$^+$).

(Step 2) Preparation of 1-(2-methylphenyl)-4-chloro-6-β,β,β-trifluoroethoxypyrrolo[3,2-c]quinoline 1-(2-Methylphenyl)-4-oxo-6-β,β,β-trifluoroethoxy-4,5-dihydropyrrolo[3,2-c]quinoline(6.1 g, 16 mmol) was dissolved in phosphoryl chloride(20 ml), then the resultant was refluxed for 2 hours. After removing the excess phosphoryl chloride by simple distillation, the residue was poured into iced water, neutralized with aqueous solution of sodium hydroxide(1N), and stirred at room temperature for 30 minutes. The resultant was extracted with dichloromethane (20 ml) for 3 times, then the organic layer was washed with water(15 ml) for 3 times, dried over anhydrous magnesium sulfate, filtered, and concentrated under reduced pressure. The residue was purified by silica gel chromatography to obtain 6.1 g of desired compound as solid in 97% of yield.

$^1$H NMR (CDCl$_3$, 200 MHz) δ 1.99(s, 3H), 4.55(q, J=8.1 Hz, 2H), 6.32–7.56(m, 9H); m/e 391(M$^+$).

(Step 3) Preparation of 1-(2-methylphenyl)-4-methylamino-6-β,β,β-trifluoroethoxypyrrolo[3,2-c]quinoline 1-(2-Methylphenyl)-4-chloro-6-β,β,β-trifluoroethoxypyrrolo[3,2-c]quinoline(600 mg, 1.5 mmol) was dissolved in aqueous solution of methylamine(40%, 10 ml) in the pressure tube, and the resultant was refluxed at 180° C. for 3 hours. After removing the excess solvent by distillation under reduced pressure, the residue was diluted in dichloromethane(20 ml), and washed with water(15 ml) for 3 times. The organic layer was dried over anhydrous magnesium sulfate, filtered, and concentrated under reduced pressure. The residue was purified by silica gel chromatography to obtain 446 mg of desired compound as solid in 77% of yield.

m.p 132–134° C.; $^1$H NMR(CDCl$_3$, 200 MHz) δ 1.89 (s, 3H), 3.28(d, J=4.9 Hz, 3H), 4.84(q, J=8.5 Hz, 2H), 4.95–5.12(m, 1H), 6.81(d, J=2.9 Hz, 1H), 6.88–6.95(m, 3H), 7.04(d, J=2.9 Hz, 1H), 7.19–7.55(m, 4H); m/e 386(M$^+$).

Example 35

Preparation of 1-(2-methylphenyl)-4-[(2-hydroxyethyl)amino]-6-β,β,β-trifluoroethoxypyrrolo[3,2-c]quinoline 1-(2-Methylphenyl)-4-chloro-6-β,β,β-trifluoroethoxypyrrolo[3,2-c]quinoline(391 mg, 1.0 mmol), prepared by the procedures of Step 1 and Step 2 in the Example 34, was dissolved in ethanolamine(10 ml) in the pressure tube, and the resultant was refluxed at 180° C. for 3 hours. After removing the excess ethanolamine by distillation under reduced pressure, the residue was diluted in dichloromethane(20 ml), and washed with water(15 ml) for 3 times. The organic layer was dried over anhydrous magnesium sulfate, filtered, and concentrated under reduced pressure. The residue was purified by silica gel chromatography to obtain 316 mg of desired compound as solid in 75% of yield.

m.p 151–153° C.; $^1$H NMR(CDCl$_3$, 200 MHz) δ 1.89(s, 3H), 2.95–3.21(m, 2H), 3.58–3.95(m, 2H), 4.62(q, J=8.3 Hz, 2H), 5.60(brs, 1H), 6.52–7.56(m, 9H); m/e 416(M$^+$).

Example 36

Preparation of 1-(2-methylphenyl)-4-[(3-hydroxypropyl)amino]-6-β,β,β-trifluoroethoxypyrrolo[3,2-c]quinoline 1-(2-Methylphenyl)-4-chloro-6-β,β,β-trifluoroethoxypyrrolo[3,2-c]quinoline(600 mg, 1.5 mmol), prepared by the procedures of Step 1 and Step 2 in the Example 34, was dissolved in 3-amino-1-propanol(10 ml) in the pressure tube, and the resultant was refluxed at 180° C. for 3 hours. After removing the excess 3-amino-1-propanol by distillation under reduced pressure, the residue was diluted in dichloromethane(20 ml), and washed with water (15 ml) for 3 times. The organic layer was dried over anhydrous magnesium sulfate, filtered, and concentrated under reduced pressure. The residue was purified by silica gel chromatography to obtain 522 mg of desired compound as solid in 81% of yield.

m.p 167–171° C.; $^1$H NMR(CDCl$_3$, 200 MHz) δ 1.76–1.89(m, 2H), 1.92(s, 3H), 2.91–3.20(m, 2H), 3.55–3.89(m, 2H), 4.63(q, J=8.3 Hz, 2H), 5.22(brs, 1H), 6.51–7.55(m, 9H); m/e 430 (M$^+$).

Example 37

Preparation of 1-(2-methylphenyl)-4-[(4-hydroxybutyl)amino]-6-β,β,β-trifluoroethoxypyrrolo[3,2-c]quinoline 1-(2-Methylphenyl)-4-chloro-6-β,β,β-trifluoroethoxypyrrolo[3,2-c]quinoline(600 mg, 1.5 mmol), prepared by the procedures of Step 1 and Step 2 in the Example 34, was added in 4-amino-1-butanol(10 ml) in the pressure tube, and refluxed at 180° C. for 3 hours. After removing the excess 4-amino-butanol by distillation under reduced pressure, the residue was diluted in dichloromethane(20 ml), and washed with water(15 ml) for 3 times. The organic layer was dried over anhydrous magnesium sulfate, filtered, and concentrated under reduced pressure. The residue was purified by silica gel chromatography to obtain 459 mg of desired compound as solid in 69% of yield.

m.p 114–116° C.; $^1$H NMR(CDCl$_3$, 200 MHz) δ 1.61–1.92(m, 4H), 1.91(s, 3H), 2.91–3.20(m, 2H), 3.55–3.89(m, 2H), 4.81(q, J=8.3 Hz, 2H), 6.55–7.55(m, 9H); m/e 443(M$^+$).

Example 38

Preparation of 1-(2-methoxyphenyl)-4-methylamino-6-β,β,β-trifluoroethoxy-2,3-dihydropyrrolo[3,2-c]quinoline (Step 1) Preparation of 1-(2-methoxyphenyl)-4-oxo-6-β,β,β-trifluoroethoxy-2,3,4,5-tetrahydropyrrolo[3,2-c]quinoline 4-Oxo-6-β,β,β-trifluoroethoxy-2,3,4,5-tetrahydrofuro[3,2-c]quinoline(5.0 g, 17.5 mmol) was dissolved in diethylene glycol(10 ml) and 2-methoxyaniline(3.6 ml, 31.6 mmol) was added under nitrogen. The reaction mixture was refluxed at 250° C. for 15 hours. After diluting the reaction mixture in brine(20 ml), the aqueous layer was extracted with dichloromethane(15 ml) for 3 times. The organic layer was washed with water(15 ml) for 3 times, dried over anhydrous magnesium sulfate, filtered, and concentrated under reduced pressure. The residue was purified with ethyl acetate as eluent by silica gel chromatography to obtain 5.3 g of desired compound as solid in 77% of yield.

m.p 200–208° C.; $^1$H NMR(CDCl$_3$, 200 MHz) δ 3.18–3.27(m, 2H), 3.27(s, 3H), 3.85–4.30(m, 2H), 4.48(q, J=7.8 Hz, 2H), 6.58–7.41(m, 7H), 8.75(brs, 1H).

(Step 2) Preparation of 1-(2-methoxyphenyl)-4-chloro-6-β,β,β-trifluoroethoxy-2,3-dihydropyrrolo[3,2-c]quinoline 1-(2-Methoxyphenyl)-4-oxo-6-β,β,β-trifluoroethoxy-2,3,4,5-tetrahydropyrrolo[3,2-c]quinoline(3.0 g, 7.7 mmol) was dissolved in phosphoryl chloride(15 ml) and the reaction mixture was refluxed for 2 hours. After removing the excess phosphoryl chloride by simple distillation, the residue was poured into iced water, neutralized with aqueous solution of sodium hydroxide(1N), and stirred at room temperature for 30 minutes. The reaction mixture was extracted with dichloromethane(20 ml) for 3 times, then the organic layer was washed with water(15 ml) for 3 times, dried over anhydrous magnesium sulfate, filtered, and concentrated under reduced pressure. The residue was purified by silica gel chromatography to obtain 2.7 g of desired compound as solid in 87% of yield.

m.p 140° C.; $^1$H NMR(CDCl$_3$, 200 MHz) δ 3.31–3.41(m, 2H), 3.72(s. 3H), 3.91–4.32(m, 2H), 4.75(q, J=8.6 Hz, 2H), 6.71–0.40(m, 7H).

(Step 3) Preparation of 1-(2-methoxyphenyl)-4-methylamino-6-β,β,β-trifluoroethoxy-2,3-dihydropyrrolo[3,2-c]quinoline 1-(2-Methoxyphenyl)-4-chloro-6-β,β,β-trifluoroethoxy-2,3-dihydropyrrolo[3,2-c]quinoline(598 mg, 1.5 mmol) was dissolved in aqueous solution of methylamine(40%, 5.0 ml) in the pressure tube, and the resultant was refluxed at 180° C. for 15 hours. The reaction mixture was dissolved in water, extracted with dichloromethane, and the organic layer was washed with water for 3 times. The organic layer was dried over anhydrous magnesium sulfate, filtered, and concentrated under reduced pressure. The residue was purified by silica gel column chromatography (ethyl acetate:hexane= 1:1) to obtain 312 mg of desired compound as solid in 53% of yield.

m.p 153° C.; $^1$H NMR(CDCl$_3$, 200 MHz) δ 2.90–3.11(m, 2H), 3.13–3.16(d, J=4.3 Hz, 3H), 3.74(s, 3H), 3.65–3.81(m, 1H), 4.21–4.30(m, 2H), 4.77(q, J=8.3 Hz, 2H), 6.65–7.25(m, 7H); m/e 403(M$^+$, 10.3), 402(22.5), 363(20.4), 333(100).

Example 39

Preparation of 1-(2-methoxyphenyl)-4-[(2-hydroxyethyl)amino]-6-β,β,β-trifluoroethoxy-2,3-dihydropyrrolo[3,2-c]quinoline 1-(2-Methoxyphenyl)-4-chloro-6-β,β,β-trifluoroethoxy-2,3-dihydropyrrolo[3,2-c]quinoline(500 mg, 1.2 mmol) was dissolved in ethanolamine(5.0 ml), and reacted at the same condition of Step 3 in the Example 38 to obtain 307 mg of desired compound as solid in 58% of yield.

m.p 153° C.; $^1$H NMR(CDCl$_3$, 200 MHz) δ 2.30–3.14(m, 2H), 3.74(s, 3H), 3.68–3.94(m, 5H), 4.25–4.33(m, 1H), 4.58(q, J=8.2 Hz, 2H), 6.67–7.32(m, 7H); m/e 433(M$^+$).

Example 40

Preparation of 1-(2-methoxyphenyl)-4-[(3-hydroxypropyl)amino]-6-β,β,β-trifluoroethoxy-2,3-dihydropyrrolo[3,2-c]quinoline 1-(2-Methoxyphenyl)-4-chloro-6-β,β,β-trifluoroethoxy-2,3-dihydro-pyrrolo[3,2-c]quinoline(500 mg, 1.2 mmol) was dissolved in 3-amino-1-propanol(5.0 ml), and reacted at the same condition of Step 3 in the Example 38 to obtain 425 mg of desired compound as solid in 77% of yield.

m.p 145° C.; $^1$H NMR(CDCl$_3$, 200 MHz) δ 1.71–1.84(m, 2H), 2.95–3.11(m, 2H), 3.52–3.85(m, 5H), 3.74(s, 3H), 4.21–4.45(m, 1H), 4.56(q, J=8.4 Hz, 2H), 6.61–7.35(m, 7H); m/e 447 (M$^+$).

Example 41

Preparation of 1-(2-methoxyphenyl)-4-[(4-hydroxybutyl)amino]-6-β,β,β-trifluoroethoxy-2,3-dihydropyrrolo[3,2-c]quinoline 1-(2-Methoxyphenyl)-4-chloro-6-β,β,β-trifluoroethoxy-2,3-dihydropyrrolo[3,2-c]quinoline(500 mg, 1.2 mmol) was dissolved in diethylene glycol(10 ml) and 4-amino-1-butanol(175 μl, 1.9 mmol) was added. It was reacted at the same condition of Step 3 in the Example 38 to obtain 120 mg of desired compound as solid in 39% of yield.

$^1$H NMR(CDCl$_3$, 200 MHz) δ 1.66–1.85(m, 4H), 2.95–3.11(m, 2H), 3.61–3.75(m, 5H), 3.75(s, 3H), 4.25–4.35(m, 1H), 4.77(q, J=8.4 Hz, 2H), 6.65–7.33(m, 7H); m/e 462(M$^+$).

Example 42

Preparation of 1-(2-methyl-4-fluorophenyl)-4-methylamino-6-β,β,β-trifluoroethoxy-2,3-dihydropyrrolo[3,2-c]quinoline (Step 1) Preparation of 1-(2-methyl-4-fluorophenyl)-4-oxo-6-β,β,β-trifluoroethoxy-2,3,4,5-tetrahydropyrrolo[3,2-c]quinoline 4-Oxo-6-β,β,β-trifluoroethoxy-2,3,4,5-tetrahydrofuro[3,2-c]quinoline(5.0 g, 17.5 mmol) was dissolved in diethylene glycol(10 ml) and 2-methyl-4-fluoroaniline(4.9 ml, 44.0 mmol) was added under nitrogen. The reaction mixture was refluxed at 250° C. for 15 hours. After diluting the reaction mixture in brine(20 ml), the aqueous layer was extracted with dichloromethane(15 ml) for 3 times. The organic layer was washed with water(15 ml), dried over anhydrous magnesium sulfate, filtered, and concentrated under reduced pressure. The residue was purified with ethyl acetate as eluent by silica gel chromatography to obtain 5.5 g of desired compound as solid in 80% of yield.

$^1$H NMR(CDCl$_3$, 200 MHz) δ 2.29(s, 3H), 3.01–3.41(m, 2H), 3.36–3.83(q, J=8.1 Hz, 1H), 3.98–4.17(m, 1H), 4.45(q, J=7.9 Hz, 2H), 6.26–7.28(m, 6H), 8.75(brs, 1H); m/e 392 (M$^+$).

(Step 2) Preparation of 1-(2-methyl-4-fluorophenyl)-4-chloro-6-β,β,β-trifluoroethoxy-2,3-dihydropyrrolo[3,2-c]quinoline 1-(2-Methyl-4-fluorophenyl)-4-oxo-6-β,β,β-trifluoroethoxy-2,3,4,5-tetrahydropyrrolo[3,2-c]quinoline (4.0 g, 10 mmol) was dissolved in phosphoryl chloride(15 ml), and refluxed for 2 hours. After removing the excess phosphoryl chloride by simple distillation, the residue was poured into iced water, neutralized with aqueous solution of sodium hydroxide(1N), and stirred at room temperature for 30 minutes. The reaction mixture was extracted with dichloromethane(20 ml), then the organic layer was washed with water(15 ml) for 3 times, dried over anhydrous magnesium sulfate, filtered, and concentrated under reduced pressure. The residue was purified by silica gel chromatography to obtain 3.1 g of desired compound as solid in 71% of yield.

$^1$H NMR(CDCl$_3$, 200 MHz) δ 3.32–3.41(m, 2H), 3.75(s. 3H), 3.91–4.35(m, 2H), 4.71(q, J=8.6 Hz, 2H), 6.71–7.40(m, 6H).

(Step 3) Preparation of 1-(2-methyl-4-fluorophenyl)-4-methylamino-6-β,β,β-trifluoroethoxy-2,3-dihydropyrrolo[3,2-c]quinoline 1-(2-Methyl-4-fluorophenyl)-4-chloro-6-β,β,β-trifluoroethoxy-2,3-dihydropyrrolo[3,2-c]quinoline(700 mg, 1.7 mmol) was dissolved in aqueous solution of methylamine(40%, 5.0 ml) and the reaction mixture was refluxed at 180° C. for 15 hours in the pressure tube. The reaction mixture was dissolved in water, extracted with dichloromethane, and the organic layer was washed with water for 3 times. The organic layer was dried over anhydrous magnesium sulfate, filtered, and concentrated under reduced pressure. The residue was purified by silica gel column chromatography(ethyl acetate:hexane=1:1) to obtain 440 mg of desired compound as solid in 64% of yield.

m.p 119–120° C.; $^1$H NMR(CDCl$_3$, 200 MHz) δ 2.32(s, 3H), 2.88–3.24(m. 5H), 3.59–3.80(m, 1H), 4.01–4.22(m, 1H), 4.22–4.38(brs, 1H), 4.81(q, J=7.9 Hz, 2H), 6.42–7.32 (m, 6H); m/e 405(M$^+$, 10.3), 404(22.5), 365(20.4), 335 (100).

Example 43

Preparation of 1-(2-methyl-4-fluorophenyl)-4-[(2-hydroxyethyl)amino]-6-β,β,β-trifluoroethoxy-2,3-dihydropyrrolo[3,2-c]quinoline 1-(2-Methyl-4-fluorophenyl)-4-chloro-6-β,β,β-trifluoroethoxy-2,3-dihydropyrrolo[3,2-c]quinoline(600 mg, 1.4 mmol) was dissolved in ethanolamine(5.0 ml). The reaction mixture was reacted at the same condition of Step 3 in the Example 42 to obtain 310 mg of desired compound as solid in 52% of yield.

m.p 142–143° C.; $^1$H NMR(CDCl$_3$, 200 MHz) δ 2.37(s, 3H), 2.92–3.28(m, 2H), 3.60–4.01(m, 5H), 4.05–4.35(m, 1H), 4.62(q, J=8.0 Hz, 2H), 6.40–7.30(m, 6H); m/e 435 (M$^+$).

Example 44

Preparation of 1-(2-methyl-4-fluorophenyl)-4-[(3-hydroxypropyl)amino]-6-β,β,β-trifluoroethoxy-2,3-dihydropyrrolo[3,2-c]quinoline 1-(2-Methyl-4-fluorophenyl)-4-chloro-6-β,β,β-trifluoroethoxy-2,3-dihydropyrrolo[3,2-c]quinoline(600 mg, 1.4 mmol) was dissolved in 3-amino-1-propanol(5.0 ml). The reaction mixture was reacted at the same condition of Step 3 in the Example 42 to obtain 520 mg of desired compound as solid in 84% of yield.

m.p 146–149° C. $^1$H NMR(CDCl$_3$, 200 MHz) δ 1.58–1.88(m, 2H), 2.32(s, 3H), 2.85–3.24(m, 2H), 3.47–3.93(m, 5H), 4.01–4.26(m, 1H), 4.57(q, J=7.9 Hz, 2H), 6.35–7.30(m, 6H); m/e 449(M$^+$).

Example 45

Preparation of 1-(2-methyl-4-fluorophenyl)-4-[(4-hydroxybutyl)amino]-6-β,β,β-trifluoroethoxy-2,3-dihydropyrrolo[3,2-c]quinoline 1-(2-Methyl-4-fluorophenyl)-4-chloro-6-β,β,β-trifluoroethoxy-2,3-dihydropyrrolo[3,2-c]quinoline(600 mg, 1.4 mmol) was dissolved in diethylene glycol(10 ml) and 4-amino-1-butanol(4 ml) was added. The reaction mixture was reacted at the same condition of Step 3 in the Example 42 to obtain 550 mg of desired compound as solid in 86% of yield.

$^1$H NMR(CDCl$_3$, 200 MHz) δ 1.54–1.92(m, 4H), 2.32(s, 3H), 2.83–3.24(m, 2H), 3.58–3.83(m, 5H), 4.05–4.25(m, 1H), 4.74(q, J=8.2 Hz, 2H), 6.45–7.30(m, 6H); m/e 463 (M$^+$).

Example 46

Preparation of 1-(2-methyl-4-fluorophenyl)-4-methylamino-6-β,β,β-trifluoroethoxypyrrolo[3,2-c]quinoline (Step 1) Preparation of 1-(2-methyl-4-fluorophenyl)-4-oxo-6-β,β,β-trifluoroethoxy-4,5-dihydropyrrolo[3,2-c]quinoline 1-(2-Methyl-4-fluorophenyl)-4-oxo-6-β,β,β-trifluoroethoxy-2,3,4,5-tetrahydropyrrolo[3,2-c]quinoline (3.7 g, 9.5 mmol), prepared by the procedures of Step 1 in the Example 42, was dissolved in diphenyl ether(20 ml) and 5%-Pd/C(600 mg) was added. The reaction mixture was refluxed for 4 hours. The reaction mixture was cooled to room temperature, and purified by silica gel chromatography to obtain 2.1 g of desired compound as solid in 58% of yield.

$^1$H NMR(CDCl$_3$, 200 MHz) δ 1.95(s, 3H), 4.50(q, J=8.1 Hz, 2H), 6.40–6.50(m, 1H), 6.79–6.85(m, 2H), 6.92(d, J=3 Hz, 1H), 7.05–7.19(m, 3H), 7.40–7.47(m, 1H), 8.99(br s, 1H); m/e 391(M$^+$+1, 24.5), 390(M$^+$, 87.3), 390(67.3), 322 (100), 307(14.9).

(Step 2) Preparation of 1-(2-methyl-4-fluorophenyl)-4-chloro-6-β,β,β-trifluoroethoxypyrrolo[3,2-c]quinoline 1-(2-Methyl-4-fluorophenyl)-4-oxo-6-β,β,β-trifluoroethoxy-4,5-dihydropyrrolo[3,2-c]quinoline(2.0 g, 5.1 mmol) was dissolved in phosphoryl chloride(20 ml), and the resultant was refluxed for 2 hours. After removing the excess phosphoryl chloride by simple distillation, the residue was poured into iced water, neutralized with aqueous solution of sodium hydroxide(1N), and stirred at room temperature for 30 minutes. The resultant was extracted with dichloromethane (20 ml) for 3 times, then the organic layer was washed with water(15 ml) for 3 times, dried over anhydrous magnesium sulfate, filtered, and concentrated under reduced pressure. The residue was purified by silica gel chromatography to obtain 2.0 g of desired compound as solid in 97% of yield.

$^1$H NMR(CDCl$_3$, 200 MHz) δ 8,91.92(s, 3H), 4.82(q, J=7.9 Hz, 2H), 6.77–6.85(m, 1H), 6.99(q, J=3.2 Hz, 1H), 7.08–7.26(m, 5H), 7.40–7.51(m, 1H); m/e 411(M$^+$+2, 8.9), 410(M$^+$+1, 8.5), 409(M$^+$, 8.0), 339(100), 311(26.7).

(Step 3) Preparation of 1-(2-methyl-4-fluorophenyl)-4-methylamino-6-β,β,β-trifluoroethoxypyrrolo[3,2-c]quinoline 1-(2-Methyl-4-fluorophenyl)-4-chloro-6-β,β,β-trifluoroethoxypyrrolo[3,2-c]quinoline(970 mg, 2.4 mmol) was dissolved in aqueous solution of methylamine(40%, 10 ml) in the pressure tube, and the resultant was refluxed at 180° C. for 3 hours. After removing the solvent by distillation under reduced pressure, the residue was diluted in dichloromethane(20 ml), and washed with water(15 ml) for 3 times. The organic layer was dried over anhydrous magnesium sulfate, filtered, and concentrated under reduced pressure. The residue was purified by silica gel chromatography to obtain 810 mg of desired compound as solid in 85% of yield.

$^1$H NMR(CDCl$_3$, 200 MHz) δ 1.88(s, 3H), 3.27(s. 3H), 4.85(q, J=8.3 Hz, 2H), 5.0(brs, NH), 6.60–6.69(m, 2H), 6.82(t, J=2.9 Hz, 1H), 6.95(d, J=3.1 Hz, 1H), 7.10–7.21(m, 3H), 7.32–7.42(m, 1H); m/e 404(M$^+$+1, 11.1), 403(M$^+$, 50.5), 334(100), 305(20.2).

Example 47

Preparation of 1-(2-methyl-4-fluorophenyl)-4 -[(2-hydroxyethyl)amino]-6-β,β,β-trifluoroethoxypyrrolo[3,2-c]quinoline 1-(2-Methyl-4-fluorophenyl)-4-chloro-6-β,β,β-trifluoroethoxypyrrolo[3,2-c]quinoline(700 mg, 1.7 mmol), prepared by the procedures of Step 1 and Step 2 in the Example 46, was dissolved in ethanolamine(10 ml) in the pressure tube, and the resultant was refluxed at 180° C. for 3 hours. After removing the excess ethanolamine by distillation under reduced pressure, the residue was diluted in dichloromethane(20 ml), and washed with water(15 ml). The organic layer was dried over anhydrous magnesium sulfate, filtered, and concentrated under reduced pressure. The residue was purified by silica gel chromatography to obtain 600 mg of desired compound as solid in 81% of yield.

¹H NMR(CDCl₃, 200 MHz) δ 2.19(s, 3H), 3.82–3.89(m, 2H), 3.95–4.02(m, 2H), 4.65(q, J=8.2 Hz, 2H), 5.69(brs, 1H), 6.61(d, J=6.1 Hz, 1H), 6.71(d, J=3.2 Hz, 1H), 6.88(t, J=2.9 Hz, 1H), 7.03(d, J=3.1 Hz, 1H), 7.10–7.18(m, 1H), 7.40–7.49(m, 1H); m/e 434(M⁺, 25.5), 415(19.8), 321(100).

Example 48

Preparation of 1-(2-methyl-4-benzyloxyphenyl)-4-[(2-hydroxyethyl)amino]-6-β,β,β-trifluoroethoxy-2,3-dihydropyrrolo[3,2-c]quinoline (Step 1) Preparation of 1-(2-methyl-4-benzyloxyphenyl)-4-oxo-6-β,β,β-trifluoroethoxy-2,3,4,5-tetrahydropyrrolo[3,2-c]quinoline 4-Oxo-6-β,β,β-trifluoroethoxy-2,3,4,5-tetrahydrofuro[3,2-c]quinoline(5.7 g, 20.0 mmol) was dissolved in diethylene glycol(70 ml) and crude 4-benzyloxy-2-methyl aniline(5.6 g, 26.0 mmol) was added. The reaction mixture was refluxed at 250° C. for 15 hours. The reaction mixture was dissolved in water, extracted with dichloromethane, and the organic layer was washed with water for 3 times. The organic layer was dried over anhydrous magnesium sulfate, filtered, and concentrated under reduced pressure. The residue was purified by silica gel column chromatography(ethyl acetate:dichloromethane=1:1) to obtain 4.5 g of desired compound as solid in 47% of yield.

¹H NMR(CDCl₃, 200 MHz) δ 2.25(s, 3H), 3.55–3.81(m, 3H), 3.97–4.19(m, 1H), 4.45(q, J=9.5 Hz, 2H), 5.11(s, 2H), 6.42(d, J=8.1 Hz, 1H), 6.73(t, J=8.3 Hz, 1H), 6.95–7.45(m, 9H), 8.75(brs, 1H); m/e 480(M⁺, 27.4), 390(23.2), 389 (87.2), 277(11.2), 91(100).

(Step 2) Preparation of 1-(2-methyl-4-benzyloxyphenyl)-4-chloro-6-β,β,β-trifluoroethoxy-2,3-dihydropyrrolo[3,2-c]quinoline 1-(2-Methyl-4-benzyloxyphenyl)-4-oxo-6-β,β,β-trifluoroethoxy-2,3,4,5-tetrahydropyrrolo[3,2-c]quinoline (2.7 g, 5.6 mmol) was mixed with phosphoryl chloride(15 ml), and stirred at 110° C. for 30 minutes. After removing the excess phosphoryl chloride by distillation, the residue was dissolved in dichloromethane (50 ml), neutralized with aqueous solution of sodium bicarbonate, and stirred at room temperature for 30 minutes. The reaction mixture was extracted with dichloromethane, and the organic layer was washed with water for 3 times. The organic layer was dried over anhydrous magnesium sulfate, filtered, and concentrated under reduced pressure. The residue was purified by silica gel column chromatography(ethyl acetate:hexane= 1:10) to obtain 1.7 g of desired compound as solid in 60% of yield.

¹H NMR(CDCl₃, 200 MHz) δ 2.21(s, 3H), 3.25–3.48(m, 2H), 3.92(q, J=9.1 Hz, 1H), 4.01–4.21(m, 1H), 4.85(q, J=8.6 Hz, 2H), 5.12(s, 2H), 6.63(d, J=8.5 Hz, 1H), 6.81–6.99(m, 3H), 7.05–7.21(m, 2H), 7.25–7.51(m, 5H); m/e 501(M⁺, 4.7), 500(10.4), 499(6.2), 498(19.4), 429(41.2), 407(35.9), 91(100).

(Step 3) Preparation of 1-(2-methyl-4-benzyloxyphenyl)-4-[(2-hydroxyethyl)amino]-6-β,β,β-trifluoroethoxy-2,3-dihydropyrrolo[3,2-c]quinoline 1-(2-Methyl-4-benzyloxyphenyl)-4-chloro-6-β,β,β-trifluoroethoxy-2,3-dihydropyrrolo[3,2-c]quinoline(749 mg, 1.5 mmol) was dissolved in ethanolamine(10 ml), and the resultant was refluxed at 180° C. for 15 hours. The reaction mixture was dissolved in water, extracted with dichloromethane, and the organic layer was washed with water for 3 times. The organic layer was dried over anhydrous magnesium sulfate, filtered, and concentrated under reduced pressure. The residue was purified by silica gel column chromatography(ethyl acetate) to obtain 650 mg of desired compound as solid in 83% of yield.

m.p 65–67° C.; ¹H NMR(CDCl₃, 200 MHz) δ 2.22(s, 3H), 2.89–3.15(m, 2H), 3.55–3.76(m, 2H), 3.78(q, J=9.5 Hz, 1H), 3.80–3.92(m, 2H), 4.01–4.18(m, 1H), 4.52(q, J=8.5 Hz, 2H), 4.73(brs, 1H), 5.03(s, 2H), 6.48(d, J=7.1 Hz, 1H), 6.65(t, J=7.7 Hz, 1H), 6.77(dd, J₁=8.7, J₂=2.9 Hz, 1H), 6.87–6.94(m, 2H), 7.01(d, J=8.6 Hz, 1H), 7.29–7.52(m, 5H); m/e 480(41), 479(79), 388(97), 91(100).

Example 49

Preparation of 1-(2-methyl-4-methoxyphenyl)-4-methylamino-6-β,β,β-trifluoroethoxy-2,3-dihydropyrrolo[3,2-c]quinoline (Step 1) Preparation of 1-(2-methyl-4-methoxyphenyl)-4-oxo-6-β,β,β-trifluoroethoxy-2,3,4,5-tetrahydropyrrolo[3,2-c]quinoline 4-Oxo-6-β,β,β-trifluoroethoxy-2,3,4,5-tetrahydrofuro[3,2-c]quinoline(5.0 g, 18 mmol) was dissolved in diethylene glycol(20 ml) and 2-methyl-4-methoxyaniline(5.7 ml, 44 mmol) was added under nitrogen. The reaction mixture was refluxed at 250° C. for 15 hours. After diluting the reaction mixture in brine(20 ml), the aqueous layer was extracted with dichloromethane(25 ml) for 3 times. The organic layer was washed with water(15 ml), dried over anhydrous magnesium sulfate, filtered, and concentrated under reduced pressure. The residue was purified with ethyl acetate as eluent by silica gel chromatography to obtain 4.7 g of desired compound as solid in 65% of yield.

¹H NMR(CDCl₃, 200 MHz) δ 2.28(s, 3H), 3.22(m, 2H), 3.71–3.89(m, 1H), 3.86(s, 3H), 4.08(m, 1H), 4.48(q, J=7.9 Hz, 2H), 6.42(d, J=8.1 Hz, 1H), 6.70–6.83(m, 3H), 6.88(d, J=2.9 Hz, 1H), 7.09(d, J=8.5 Hz, 1H), 8.74(brs, 1H); m/e 404(M⁺, 100), 403(75.1), 402(25.1), 335(12.5).

(Step 2) Preparation of 1-(2-methyl-4-methoxyphenyl)-4-chloro-6-β,β,β-trifluoroethoxy-2,3-dihydropyrrolo[3,2-c]quinoline 1-(2-Methyl-4-methoxyphenyl)-4-oxo-6-β,β,β-trifluoroethoxy-2,3,4,5-tetrahydropyrrolo[3,2-c]quinoline (3.0 g, 7.4 mmol) was dissolved in phosphoryl chloride(15 ml), then the resultant was refluxed for 2 hours. After removing the excess phosphoryl chloride by simple distillation, the residue was poured into iced water, neutralized with aqueous solution of sodium hydroxide(1N), and stirred at room temperature for 30 minutes. The resultant was extracted with dichloromethane (20 ml), then the organic layer was washed with water(15 ml), dried over anhydrous magnesium sulfate, filtered, and concentrated under reduced pressure. The residue was purified by silica gel chromatography to obtain 2.9 g of desired compound as solid in 93% of yield.

¹H NMR(CDCl₃, 200 MHz) δ 2.25(s, 3H), 3.32–3.39(m, 2H), 3.88(s, 3H), 4.07–4.13(m, 2H), 6.75–7.01(m, 4H), 7.15(d, J=8.4 Hz, 1H), 7.40–7.45(m, 1H); m/e 422(M⁺, 12.5), 353(100).

(Step 3) Preparation of 1-(2-methyl-4-methoxyphenyl)-4-methylamino-6-β,β,β-trifluoroethoxy-2,3-dihydropyrrolo [3,2-c]quinoline 1-(2-Methyl-4-methoxyphenyl)-4-chloro-6-β,β,β-trifluoroethoxy-2,3-dihydropyrrolo[3,2-c]quinoline(600 mg, 1.42 mmol) was dissolved in aqueous solution of methylamine(40%, 5.0 ml) in the pressure tube, and the reaction mixture was refluxed at 180° C. for 15 hours. The reaction mixture was dissolved in water, extracted with dichloromethane, and the organic layer was washed with water for 3 times. The organic layer was dried over anhydrous magnesium sulfate, filtered, and concentrated under reduced pressure. The residue was purified by silica gel column chromatography(ethyl acetate:hexane=1:2) to obtain 450 mg of desired compound as solid in 76% of yield.

m.p 121–125° C.; ¹H NMR(CDCl₃, 200 MHz) δ 2.24(s, 3H), 2.85–3.15(m, 2H), 3.15(d, J=4.5 Hz, 3H), 3.71(q, J=8.5 Hz, 1H), 3.79(s, 3H), 4.01–4.18(m, 1H), 4.18(brs, 1H), 4.78(dq, J1=3.1, J2=9.8 Hz, 2H), 6.51–6.72(m, 3H), 6.81(d, J=2.1 Hz, 1H), 6.96–7.06(m, 2H); m/e 418(M⁺, 7.2), 417 (23.3), 349(23.6), 348(100), 319(22.3).

Example 50

Preparation of 1-(2-methyl-4-methoxyphenyl)-4-[(2-hydroxyethyl)amino]-6-β,β,β-trifluoro-2,3-dihydropyrrolo[3,2-c]quinoline 1-(2-Methyl-4-methoxyphenyl)-4-chloro-6-β,β,β-trifluoroethoxy-2,3-dihydropyrrolo[3,2-c]quinoline(700 mg, 1.7 mmol) was dissolved in ethanolamine(5.0 ml), and reacted at the same condition of Step 3 in the Example 49 to obtain 580 mg of desired compound as solid in 78% of yield.

m.p 132–134° C.; ¹H NMR(CDCl₃, 200 MHz) δ 2.28(s, 3H), 3.05–3.07(m, 2H), 3.64–3.82(m, 3H), 3.86(s, 3H), 3.88–3.97(m, 2H), 4.10–4.17(m, 1H), 4.58(q, J=8.9 Hz, 2H), 4.80(brs, 1H), 6.52(d, J=2.5 Hz, 1H), 6.70–6.79(m, 2H), 6.85(d, J=2.5 Hz, 1H), 6.95(d, J=3.1 Hz, 1H), 7.05(d, J=3.1 Hz, 1H); m/e 447(M+, 27.5), 430(34.2), 416(19.7), 402 (100).

Example 51

Preparation of 1-(2-methyl-4-methoxyphenyl)-4-[(3-hydroxypropyl)amino]-6-β,β,β-trifluoroethoxy-2,3-dihydropyrrolo[3,2-c]quinoline 1-(2-Methyl-4-methoxyphenyl)-4-chloro-6-β,β,β-trifluoroethoxy-2,3-dihydropyrrolo[3,2-c]quinoline(700 mg, 1.7 mmol) was dissolved in 3-amino-1-propanol(5.0 ml), and reacted at the same condition of Step 3 in the Example 49 to obtain 470 mg of desired compound as solid in 60% of yield.

m.p 151–153° C.; ¹H NMR(CDCl₃, 200 MHz) δ 1.71–1.79(m, 2H), 2.27(s, 3H), 3.01–3.11(m, 2H), 3.55–3.63(m, 2H), 3.74–3.90(m, 3H), 3.82(s, 3H), 4.10–4.16(m, 1H), 4.42(brs, 1H), 4.58(q, J=9.2 Hz, 2H), 6.50(d, J=2.7 Hz, 1H), 6.60–6.76(m, 2H), 6.83(d, J=2.7 Hz, 1H), 6.90(d, J=3.1 Hz, 1H), 7.02(d, J=3.2 Hz, 1H); m/e 461(M⁺, 21.2), 430(48.9), 416(100), 402(78.4).

Example 52

Preparation of 1-(2-methyl-4-methoxyphenyl)-4-methylamino-6-β,β,β-trifluoroethoxypyrrolo[3,2-c]quinoline 1-(2-Methyl-4-methoxyphenyl)-4-methylamino-6-β,β,β-trifluoro-ethoxy-2,3-dihydropyrrolo [3,2-c]quinoline(250 mg, 0.60 mmol) was dissolved in diphenyl ether(10 ml) and 10%-Pd/C(42 mg) was added. The reaction mixture was refluxed at 270° C. for 2 hours. The reaction mixture was purified by silica gel column chromatography(ethyl acetate:dichloromethane=1:3) to obtain 190 mg of desired compound as solid in 77% of yield.

m.p 118–120° C.; ¹H NMR(CDCl₃, 200 MHz) δ 1.88(s, 3H), 3.31(s, 3H), 3.93(s, 3H), 4.88(q, J=9.8 Hz, 2H), 5.03 (brs, 1H), 6.64(d, J=2.9 Hz, 1H), 6.72(d, J=8.0 Hz, 1H), 6.81(d, J=8.0 Hz, 1H), 6.87(d, J=3.1 Hz, 1H), 6.92(s, 1H), 6.97(d, J=2.9 Hz, 1H), 7.06–7.35(m, 2H); m/e 416(M⁺, 6.4), 415(28.1), 346(100), 317(18.7), 173(8.1).

Example 53

Preparation of 1-(2-methyl-4-hydroxyphenyl)-4-methylamino-6-β,β,β-trifluoroethoxy-2,3-dihydropyrrolo[3,2-c]quinoline (Step 1) Preparation of 1-(2-methyl-4-hydroxyphenyl)-4-oxo-6-β,β,β-trifluoroethoxy-2,3,4,5-tetrahydropyrrolo[3,2-c]quinoline 4-Oxo-6-β,β,β-trifluoroethoxy-2,3,4,5-tetrahydropyrrolo [3,2-c]quinoline(4.6 g, 16 mmol) was dissolved in diethylene glycol(30 ml) and 4-amino-m-cresol(2.2 g, 18 mmol) was added under nitrogen. The reaction mixture was refluxed at 250° C. for 20 hours. The reaction mixture was diluted in brine(20 ml), and the aqueous layer was extracted with dichloromethane(15 ml) for 3 times. The organic layer was washed with water(15 ml) for 3 times, dried over anhydrous magnesium sulfate, filtered, and concentrated under reduced pressure. The residue was purified with ethyl acetate as eluent by silica gel chromatography to obtain 5.2 g of desired compound as solid in 83% of yield.

m.p 235–237° C.; ¹H NMR(CDCl₃, 200 MHz) δ 2.19(s, 3H), 3.06–3.29(m, 2H), 3.80(q, J=9.1 Hz, 1H), 3.93–4.12(m, 1H), 4.44(q, J=8.3 Hz, 2H), 6.46(d, J=8.5 Hz, 1H), 6.67–6.85(m, 5H), 6.96(d, J=8.5 Hz, 1H), 8.71(brs, 1H), 8.85(brs, 1H); m/e 391(M⁺+1, 19.1), 390(M⁺, 94.0), 389 (100), 388(65.5), 321(17.8), 305(9.7).

(Step 2) Preparation of 1-(2-methyl-4-methanesulfoxyphenyl)-4-oxo-6-β,β,β-trifluoroethoxy-2,3,4,5-tetrahydropyrrolo[3,2-c]quinoline 1-(2-Methyl-4-hydroxyphenyl)-4-oxo-6-β,β,β-trifluoroethoxy-2,3,4,5-tetrahydropyrrolo[3,2-c]quinoline (2.5 g, 6.4 mmol) was dissolved in dichloromethane, triethylamine(2.2 ml, 16.0 mmol), and methanesulfonyl chloride(1.1 ml, 13.5 mmol) was added at −78° C. The reaction mixture was stirred for 3 hours, then slowly warmed up to −10° C., and stirred for 1 hours. The reaction mixture was extracted with dichloromethane, and the organic layer was washed with water for 3 times. The organic layer was dried over anhydrous magnesium sulfate, filtered, and concentrated under reduced pressure. The residue was crystallized in dichloromethane/hexane to obtain 2.3 g of desired compound as solid in 75% of yield.

m.p 91–93° C.; ¹H NMR(CDCl₃, 200 MHz) δ 2.36(s, 3H), 3.21(s, 3H), 3.10–3.39(m, 2H), 3.61–3.84(m, 1H), 4.06–4.22(m, 1H), 4.47(q, J=8.5 Hz, 1H), 6.37(d, J=8.1 Hz, 1H), 6.71–6.92(m, 2H), 7.12(s, 1H), 7.08–7.17(m, 2H), 7.27(s, 1H), 8.82(brs, 1H); m/e 468(M⁺, 41.2), 391(21.1), 389(100), 277(16.2).

(Step 3) Preparation of 1-(2-methyl-4-methanesulfoxyphenyl)-4-chloro-6-β,β,β-trifluoroethoxy-2,3-dihydropyrrolo[3,2-c]quinoline 1-(2-Methyl-4-methanesulfoxyphenyl)-4-oxo-6-β,β,β-trifluoroethoxy-2,3-dihydropyrrolo[3,2-c]quinoline(1.2 g, 2.3 mmol) was mixed with phosphoryl chloride(10 ml), and stirred at 110° C. for 30 minutes. After removing the excess phosphoryl chloride by distillation, the residue was dissolved in dichloromethane(20 ml), neutralized with aqueous solution of sodium bicarbonate, and stirred at room temperature for 30 minutes. The resultant was extracted with dichloromethane, and the organic layer was washed with water for 3 times, dried over anhydrous magnesium sulfate, filtered, and concentrated under reduced pressure. The residue was purified by silica gel column chromatography(ethyl acetate:hexane=1:5) to obtain 0.9 g of desired compound as solid in 76% of yield.

m.p 55–57° C.; ¹H NMR(CDCl₃, 200 MHz) δ 2.32(s, 3H), 3.23(s, 3H), 3.25–3.47(m, 2H), 3.90(q, J=9.2 Hz, 1H), 4.06–4.27(m, 1H), 4.75(q, J=8.2 Hz, 2H), 6.57(d, J=8.9 Hz, 1H), 6.95(t, J=8.1 Hz, 1H), 7.13(d, J=8.9 Hz, 1H), 7.18(s, 1H), 7.15–7.33(m, 2H); m/e 488(M⁺+2, 12.2), 487(M⁺+1, 14.2), 486(M⁺, 32.5), 419(46.8), 418(33.1), 417(100), 407 (15.8), 309(21.1).

(Step 4) Preparation of 1-(2-methyl-4-hydroxyphenyl)-4-methylamino-6-β,β,β-trifluoroethoxy-2,3-dihydropyrrolo [3,2-c]quinoline 1-(2-Methyl-4-methanesulfoxyphenyl)-4-chloro-6-β,β,β-trifluoroethoxy-2,3-dihydropyrrolo[3,2-c]quinoline(650 mg, 1.3 mmol) was dissolved in aqueous solution of methylamine(40%, 5.0 ml), and the resultant was refluxed at 180° C. for 15 hours. The reaction mixture was dissolved in water, extracted with dichloromethane, and the organic layer was washed with water for 3 times. The organic layer was dried over anhydrous magnesium sulfate, filtered, and concentrated under reduced pressure. The residue was purified by silica gel column chromatography(ethyl acetate:hexane= 1:1) to obtain 250 mg of desired compound as solid in 47% of yield.

$^1$H NMR(CDCl$_3$, 200 MHz) δ 2.21(s, 3H), 2.95–3.15(m, 2H), 3.17(s, 3H), 3.55–3.71(M, 1H), 4.01–4.17(M, 1h), 4.69(q, J=9.1 Hz, 1H), 6.55–7.07(m, 6H); m/e 404(M$^+$, 2.7), 347(25.0), 132(29.2), 83(100).

Example 54

Preparation of 1-(2-methyl-4-hydroxyphenyl)-4-[(2-hydroxyethyl)amino]-6-β,β,β-trifluoroethoxy-2,3-dihydropyrrolo[3,2-c]quinoline 1-(2-Methyl-4-methanesulfoxyphenyl)-4-chloro-6-β,β,β-trifluoroethoxy-2,3-dihydropyrrolo[3,2-c]quinoline(650 mg, 1.3 mmol) was dissolved in ethanolamine(5.0 ml), and reacted at the same condition of Step 4 in the Example 53 to obtain 440 mg of desired compound as solid in 78% of yield.

m.p 215–217° C.; $^1$H NMR(CDCl$_3$, 200 MHz) δ 2.19(s, 3H), 2.95–3.15(m, 2H), 3.65–3.75(m, 2H), 3.79(q, J=10.6 Hz, 1H), 3.79–3.92(m, 2H), 4.02–4.19(m, 1H), 4.57(q, J=8.6 Hz, 2H), 5.09(brs, 1H), 6.51–6.72(m, 3H), 6.80(d, J=2.5 Hz, 1H), 6.92(d, J=8.5 Hz, 2H); m/e 434(M$^+$, 12.5), 403(5.3), 388(100), 320(38).

Example 55

Preparation of 1-(2-methyl-4-hydroxyphenyl)-4-[(2-hydroxyethyl)amino]-6-β,β,β-trifluoroethoxypyrrolo[3,2-c]quinoline (Step 1) Preparation of 1-(2-methyl-4-methanesulfoxyphenyl)-4-oxo-6-β,β,β-trifluoroethoxy-4,5-dihydropyrrolo[3,2-c]quinoline 1-(2-Methyl-4-methanesulfoxyphenyl)-4-oxo-6-β,β,β-trifluoroethoxy-2,3,4,5-tetrahydropyrrolo[3,2-c]quinoline (470 mg, 1.0 mmol) was dissolved in diphenyl ether(10 ml) and 10%-Pd/C(100 mg) was added. The reaction mixture was refluxed at 270° C. for 1 hour. The reaction mixture was purified by silica gel column chromatography(ethyl acetate:dichloromethane=1:1) to obtain 370 mg of desired compound as solid in 79% of yield.

$^1$H NMR(CDCl$_3$, 200 MHz) δ 1.99(s, 3H), 3.31(s, 3H), 4.51(q, J=8.0 Hz, 2H), 6.38–6.47(m, 1H), 6.82–6.87(m, 1H), 6.93(d, J=1.7 Hz, 1H), 7.11(d, J=1.7 Hz, 1H), 7.25–7.55(m, 4H), 8.96(brs, 1H); m/e 468(M$^+$, 9.7), 467(27.5), 466(100), 398(6.4), 387(9.6), 318(9.2).

(Step 2) Preparation of 1-(2-methyl-4-methanesulfoxyphenyl)-4-chloro-6-β,β,β-trifluoroethoxypyrrolo[3,2-c]quinoline 1-(2-Methyl-4-methanesulfoxyphenyl)-4-oxo-6-β,β,β-trifluoroethoxy-4,5-dihydropyrrolo[3,2-c]quinoline(370 mg, 0.8 mmol) was mixed with phosphoryl chloride(5ml) and stirred at 110° C. for 30 minutes. After removing the excess phosphoryl chloride by distillation, the residue was dissolved in dichloromethane(20 ml), neutralized with aqueous solution of sodium bicarbonate, and stirred at room temperature for 30 minutes. The resultant was extracted with dichloromethane, and the organic layer was washed with water for 3 times, dried over anhydrous magnesium sulfate, filtered, and concentrated under reduced pressure. The residue was purified by silica gel column chromatography(ethyl acetate:hexane=1:5) to obtain 350 mg of desired compound as solid in 91% of yield.

m.p 155–157° C.; $^1$H NMR(CDCl$_3$, 200 MHz) δ 1.93(s, 3H), 3.31(s, 3H), 4.79(q, J=8.6 Hz, 1H), 6.71–6.82(m, 1H), 6.93(d, J=3.2 Hz, 1H), 7.12(d, J=3.2 Hz, 1H), 7.12–7.23(m, 2H), 7.31–7.52(m, 3H); m/e 484(M$^+$, 7.3), 417(34.4), 416 (27.4), 415(100), 414(47.4), 336(30.7), 307(30.1), 264 (13.2).

(Step 3) Preparation of 1-(2-methyl-4-hydroxyphenyl)-4-[(2-hydroxyethyl)amino]-6-β,β,β-trifluoroethoxypyrrolo[3,2-c]quinoline 1-(2-Methyl-4-methanesulfoxyphenyl)-4-chloro-6-β,β,β-trifluoro-ethoxypyrrolo[3,2-c]quinoline(180 mg, 0.37 mmol) was dissolved in ethanolamine(5.0 ml), and the resultant was refluxed at 180° C. for 15 hours. The reaction mixture was dissolved in water, extracted with dichloromethane, and the organic layer was washed with water for 3 times. The organic layer was dried over anhydrous magnesium sulfate, filtered, and concentrated under reduced pressure. The residue was purified by silica gel column chromatography(ethyl acetate:hexane=1:1) to obtain 131 mg of desired compound as solid in 82% of yield.

m.p 209–210° C.; $^1$H NMR(CDCl$_3$, 200 MHz) δ 1.92(s, 3H), 3.81–3.91(m, 2H), 3.96–4.05(m, 2H), 4.61(q, J=8.7 Hz, 2H), 6.55–6.65(m, 2H), 6.66–6.72(m, 3H), 6.85–6.98(m, 3H); m/e 431(M$^+$, 21.5), 430(11.1), 412(10.3), 388(33.3), 362(16.6), 332(29.9), 318(100).

Example 56

Preparation of 1-(2-methyl-4-hydroxyphenyl)-4-[(3-hydroxypropyl)amino]-6-β,β,β-trifluoroethoxypyrrolo[3,2-c]quinoline 1-(2-Methyl-4-methanesulfoxyphenyl)-4-chloro-6-β,β,β-trifluoro-ethoxypyrrolo[3,2-c]quinoline(160 mg, 0.33 mmol) was dissolved in 3-amino-1-propanol(5.0 ml), and reacted at the same condition of Step 3 in the Example 55 to obtain 100 mg of desired compound as solid in 68% of yield.

m.p 205–207° C.; $^1$H NMR(CDCl$_3$, 200 MHz) δ 1.71–1.89(m, 2H), 2.47(s, 3H), 3.52–3.63(m, 2H), 3.85–3.98(m, 2H), 4.61(q, J=8.5 Hz, 2H), 5.79(brs, 1H), 6.62–7.02(m, 7H), 7.14(d, J=8.1 Hz, 1H), 9.16(brs, 1H); m/e 445(M$^+$, 37.9), 414(77.2), 401(87.9), 376(29.3), 332(100), 318(58.8).

Example 57

Preparation of 1-(2-methylphenyl)-4-[(2-hydroxyethyl)amino]-6-β,β,γ,γ,γ-6-pentafluoropropyloxy-2,3-dihydropyrrolo[3,2-c]quinoline (Step 1) Preparation of 2-β,β,γ,γ,γ-pentafluoropropyloxynitrobenzene Sodium hydride(60%, 2.8 g, 70 mmol) was put in flask under nitrogen and purified tetrahydrofuran(150 ml) was added. After slow addition of 1H,1H-pentafluoropropanol (11.4 g, 76 mmol) at 0° C., the reaction mixture was stirred at 0° C. for 10 minutes, added 2-chloronitrobenzene(10 g, 64 mmol) in dropwise, and stirred again at 10° C. for 72 hours. The reaction mixture was dissolved in water, extracted with ether, and the organic layer was washed with water for 3 times. The organic layer was dried over anhydrous magnesium sulfate, filtered, and concentrated under reduced pressure to obtain 17 g of desired compound as solid in 96% of yield.

¹H NMR(CDCl₃, 200 MHz) δ 4.57(t, J=9.6 Hz, 2H), 7.09–7.30(m, 2H), 7.55–7.66(m, 1H), 7.85–7.95(m, 1H); m/e 272(M⁺+1, 12.3), 271(M⁺, 23.1), 119(55.4), 84(100).

(Step 2) Preparation of 2-β,β,γ,γ,γ-pentafluoropropyloxyaniline

Iron powder(16.5 g, 300 mmol) was added to aqueous solution of acetic acid(5%, 200 ml), and stirred at 80° C. for 30 minutes. Hereto was slowly added 2-β,β,γ,γ,γ-pentafluoropropyloxynitrobenzene(16.4 g, 60 mmol) in acetic acid, and stirred at 100° C. for 30 minutes. The reaction mixture was extracted with ether, neutralized with aqueous solution of sodium hydroxide(1N), and concentrated under reduced pressure to obtain 12.5 g of desired compound as solid in 85% of yield.

¹H NMR(CDCl₃, 200 MHz) δ 3.84(brs, 2H), 4.45(t, J=9.3 Hz, 2H), 6.71–6.84(m, 2H), 6.87–6.97(m, 2H); m/e 241(M⁺, 78.5), 108(56.4), 119(34.2), 84(100).

(Step 3) Preparation of 4-oxo-6-β,β,γ,γ,γ-pentafluoropropyloxy-2,3,4,5-tetrahydrofuro[3,2-c]quinoline 2-β,β,γ,γ,γ-Pentafluoropropyloxyaniline(12.5 g, 52 mmol) was dissolved in diphenyl ether(75 ml) and diethyl-2-(ethoxyethyl)malonate(12.6 g, 54 mmol) was added at room temperature. The reaction mixture was stirred at 220° C. for 7 hours, warmed up to 270° C., and refluxed for 24 hours in Dean-Stark apparatus. After removing diphenyl ether by distillation under reduced pressure, the residue was crystallized in dichloromethane/hexane to obtain 7.5 g of desired compound as solid in 43% of yield.

¹H NMR(CDCl₃, 200 MHz) δ 2.35 (s, 3H), 3.11–3.42 (m, 2H), 3.76–3.92 (m, 1H), 4.11–4.25 (m, 1H), 4.55 (q, J=9.1 Hz, 2H), 6.37–7.41 (m, 7H), 8.75 (brs, 1H); m/e 335(M⁺, 12.1), 334(11.2), 224(100).

(Step 4) Preparation of 1-(2-methylphenyl)-4-oxo-6-β,β,γ,γ,γ-pentafluoropropyloxy-2,3,4,5-tetrahydropyrrolo[3,2-c]quinoline 4-Oxo-β,β,γ,γ,γ-pentafluoropropyloxy-2,3,4,5-tetrahydrofuro[3,2-c]quinoline(7.5 g, 22 mmol) was dissolved in diethylene glycol(30 ml) and 2-methylaniline(30 ml) was added under nitrogen. The resultant was refluxed for 15 hours. After diluting the above mixture in brine(50 ml), the resultant was extracted with dichloromethane(50 ml) for 3 times. The organic layer was washed with water(50 ml) for 3 times, dried over anhydrous magnesium sulfate, filtered, and concentrated. The residue was crystallized in dichloromethane/hexane to obtain 7.3 g of desired compound as solid in 78% of yield.

¹H NMR(CDCl₃, 200 MHz) δ 1.95(s, 3H), 3.36–3.43(m, 2H), 3.92–4.04(m, 1H), 4.16–4.20(m, 1H), 4.56(t, J=9.1 Hz, 2H), 6.40–6.46(m, 1H), 6.81(d, J=5.4 Hz, 2H), 6.95(d, J=3.2 Hz, 1H), 7.09(d, J=3 Hz, 1H), 7.35–7.56(m, 4H); m/e 421(M⁺+1, 15.7), 420(M⁺, 35.0), 302(21.4), 272(100).

(Step 5) Preparation of 1-(2-methylphenyl)-4-chloro-6-β,β,γ,γ,γ-pentafluoropropyloxy-2,3-dihydropyrrolo[3,2-c]quinoline 1-(2-Methylphenyl)-4-oxo-6-β,β,γ,γ,γ-pentafluoropropyloxy-2,3,4,5-tetrahydropyrrolo[3,2-c]quinoline (3.8 g, 9.0 mmol) was dissolved in phosphoryl chloride(25 ml), then stirred for 2 hours. After removing the excess phosphoryl chloride by simple distillation, the residue was poured into iced water, neutralized with aqueous solution of sodium hydroxide(1N), and stirred at room temperature for 30 minutes. The resultant was extracted with dichloromethane(20 ml) for 3 times, and the organic layer was washed with water(15 ml) for 3 times, dried over anhydrous magnesium sulfate, filtered, and concentrated under reduced pressure. The residue was purified by silica gel column chromatography to obtain 3.4 g of desired compound as solid in 86% of yield.

¹H NMR(CDCl₃, 200 MHz) δ 2.25(s, 3H), 3.38–3.43(m, 2H), 3.95(dq, J₁=9.2 Hz, J₂=10.2 Hz, 1H), 4.16–4.20(m, 1H), 4.83(t, J=9.6 Hz, 2H), 6.56(d, J=8.4 Hz, 1H), 6.87(t, J=3.6 Hz, 1H), 7.06–7.40(m, 5H); m/e 444(M⁺+2, 9.8), 443(M⁺+1, 9.9), 442(M⁺, 26.5), 323(100).

(Step 6) Preparation of 1-(2-methylphenyl)-4-[(2-hydroxyethyl)amino]-6-β,β,γ,γ,γ-pentafluoropropyloxy-2,3-dihydropyrrolo[3,2-c]quinoline 1-(2-Methylphenyl)-4-chloro-6-β,β,γ,γ,γ-pentafluoropropyloxy-2,3-dihydropyrrolo[3,2-c]quinoline (600 mg, 1.4 mmol) was dissolved in ethanolamine(5.0 ml), and the resultant was refluxed at 180° C. for 15 hours in the pressure tube. The reaction mixture was dissolved in water, extracted with dichloromethane, and the organic layer was washed with water for 3 times. The organic layer was dried over anhydrous magnesium sulfate, filtered, and concentrated under reduced pressure. The residue was purified by silica gel column chromatography(ethyl acetate:hexane= 1:1) to obtain 420 mg of desired compound as solid in 67% of yield.

m.p 146–147° C.; ¹H NMR(CDCl₃, 200 MHz) δ 2.31(s, 3H), 3.06–3.12(m, 2H), 3.68–3.83(m, 3H), 3.83–3.95(m, 2H), 4.16–4.20(m, 1H), 4.68(t, J=9.6 Hz, 2H), 4.80(brs, 1H), 6.49(d, J=7.1 Hz, 1H), 6.68(t, J=3.4 Hz, 1H), 6.95(d, J=7.6 Hz, 1H), 7.03(d, J=7.2 Hz, 1H), 7.18–7.35(m, 3H); m/e 468(M⁺+1, 25.1), 467(M⁺, 87.2), 450(45.2), 436(42.1), 423 (100).

Example 58

Preparation of 1-(2-methylphenyl)-4-[(3-hydroxypropyl)amino]-6-β,β,γ,γ,γ-pentafluoropropyloxy-2,3-dihydropyrrolo[3,2-c]quinoline 1-(2-Methylphenyl)-4-chloro-6-β,β,γ,γ,γ-pentafluoropropyloxy-2,3-dihydropyrrolo[3,2-c]quinoline (570 mg, 1.2 mmol) was dissolved in 3-amino-1-propanol (5.0 ml), and reacted at the same condition of Step 6 in the Example 57 to obtain 260 mg of desired compound as solid in 42% of yield.

m.p 159–161° C.; ¹H NMR(CDCl₃, 200 MHz) δ 1.72–1.80(m, 2H), 2.31(s, 3H), 3.03–3.11(m, 2H), 3.58(q, J=5.4 Hz, 2H), 3.70–3.92(m, 3H), 4.20–4.26(m, 1H), 4.43 (br s, 1H), 4.66(t, J=9.9 Hz, 2H), 6.47(d, J=8.2 Hz, 1H), 6.67(d, J=8.2 Hz, 1H), 7.05–7.11(m, 1H), 7.10–7.36(m, 3H); m/e 482(M⁺, 11.8), 481(31.9), 450(50.1), 436(58.3), 362 (31.2), 84(100).

Example 59

Preparation of 1-(2-methylphenyl)-4-[(2-hydroxyethyl)amino]-6-β,β,γ,γ,γ-pentafluoropropyloxypyrrolo[3,2-c]quinoline (Step 1) Preparation of 1-(2-methylphenyl)-4-oxo-6-β,β,γ,γ,γ-pentafluoropropyloxy-4,5-dihydropyrrolo[3,2-c]quinoline 1-(2-Methylphenyl)-4-oxo-6-β,β,γ,γ,γ-pentafluoropropyloxy-2,3,4,5-tetrahydropyrrolo[3,2-c]quinoline (2.6 g, 6.1 mmol), prepared by the procedure of Step 4 in the Example 57, was dissolved in diphenyl ether(20 ml) and 5%-Pd/C(400 mg) was added. The reaction mixture was refluxed for 4 hours, cooled to room temperature, and purified by silica gel chromatography to obtain 2.1 g of desired compound as solid in 58% of yield.

¹H NMR (CDCl₃, 200 MHz) δ 1.95(s, 3H), 4.56(t, J=9.1 Hz, 2H), 6.40–6.46(m, 1H), 6.81(d, J=5.4 Hz, 2H), 6.95(d,

J=3.2 Hz, 1H), 7.09(d, J=3.2 Hz, 1H), 7.35–7.56(m, 4H); m/e 423($M^+$+1, 23.7), 422($M^+$, 75.0), 304(24.4), 274(100).

(Step 2) Preparation of 1-(2-methylphenyl)-4-chloro-6-β,β,γ,γ,γ-pentafluoropropyloxypyrrolo[3,2-c]quinoline 1-(2-Methylphenyl)-4-oxo-6-β,β,γ,γ,γ-pentafluoropropyloxy-4,5-dihydropyrrolo[3,2-c]quinoline (1.5 g, 3.8 mmol) was dissolved in phosphoryl chloride(15 ml), then the resultant was stirred for 2 hours. After removing the excess phosphoryl chloride by simple distillation, the residue was poured into iced water, neutralized with aqueous solution of sodium hydroxide (1N), and stirred at room temperature for 30 minutes. It was extracted with dichloromethane(20 ml) for 3 times, and the organic layer was washed with water(15 ml) for 3 times, dried over anhydrous magnesium sulfate, filtered, and concentrated under reduced pressure. The residue was purified by silica gel chromatography to obtain 1.5 g of desired compound as solid in 94% of yield.

$^1$H NMR($CDCl_3$, 200 MHz) δ 1.91(s, 3H), 4.97(t, J=9.8 Hz, 2H), 6.80(d, J=6.2 Hz, 1H), 6.97(d, J=3.2 Hz, 1H), 7.05–7.22(m, 3H), 7.38–7.60(m, 4H); m/e 442($M^+$+2, 12.4), 440($M^+$, 35.1), 351(37.3), 321(100).

(Step 3) Preparation of 1-(2-methylphenyl)-4-[(2-hydroxyethyl)amino]-6-β,β,γ,γ,γ-pentafluoropropyloxypyrrolo[3,2-c]quinoline 1-(2-Methylphenyl)-4-chloro-6-β,β,γ,γ,γ-pentafluoropropyloxypyrrolo[3,2-c]quinoline(600 mg, 1.4 mmol) was dissolved in ethanolamine(5.0 ml), then stirred at 180° C. for 15 hours in the pressure tube. The reaction mixture was dissolved in water, extracted with dichloromethane, and the organic layer was washed with water for 3 times. The organic layer was dried over anhydrous magnesium sulfate, filtered, and concentrated under reduced pressure. The residue was purified by silica gel column chromatography(ethyl acetate:hexane=1:1) to obtain 560 mg of desired compound as solid in 89% of yield.

m.p 147–150° C.; $^1$H NMR($CDCl_3$, 200 MHz) δ 1.93(s, 3H), 3.86–3.91(m, 2H), 3.96–4.03 m, 2H), 4.76(t, J=9.7 Hz, 2H), 5.65(brs, 1H), 6.62(d, J=7.2 Hz, 1H), 6.71(d, J=3.6 Hz, 1H), 6.83(t, J=3.6 Hz, 1H), 6.97–7.09(m, 2H), 7.34–7.59(m, 4H); m/e 465($M^+$, 19.4), 448(13.7), 434(21.2), 420(63.2), 302(100).

Example 60

Preparation of 1-(2-methylphenyl)-4-[(3-hydroxypropyl)amino]-6-β,β,γ,γ,γ-pentafluoropropyloxypyrrolo[3,2-c]quinoline 1-(2-Methylphenyl)-4-chloro-6-β,β,γ,γ,γ-pentafluoropropyloxypyrrolo[3,2-c]quinoline(600 mg, 1.4 mmol) was dissolved in 3-amino-1-propanol(5.0 ml), and reacted at the same condition of Step 3 in the Example 59 to obtain 610 mg of desired compound as solid in 94% of yield.

m.p 163–165° C.; $^1$H NMR($CDCl_3$, 200 MHz) δ 1.85–1.93(m, 2H), 1.94(s, 3H), 3.64(t, J=7.9 Hz, 2H), 3.94–4.03(m, 2H), 4.72(t, J=9.4 Hz, 2H), 5.29(brs, 1H), 6.59(d, J=7.1 Hz, 1H), 6.69(d, J=3.2 Hz, 1H), 6.81(t, J=3.6 Hz, 1H), 6.98(d, J=7.1 Hz, 1H), 7.03(d, J=3.6 Hz, 1H), 7.35–7.59(m, 4H); m/e 480($M^+$, 9.5), 479(14.6), 448(72.1), 434(37.8), 45(100).

Example 61

Preparation of 1-(2-methylphenyl)-4-[(2-hydroxyethyl)amino]-6-β,β,β-trifluoroethoxy-2,3-dihydropyrrolo[3,2-c]quinoline.HCl salt 1-(2-Methylphenyl)-4-[(2-hydroxyethyl)amino]-6-β,β,β-trifluoroethoxy-2,3-dihydropyrrolo[3,2-c]quinoline(230 mg, 0.6 mmol) was dissolved in diethyl ether(10 ml), and injected gaseous hydrochloric acid at 0° C. for 20 minutes. After filtering the precipitate, the filter cake was washed with diethyl ether and dried under reduced pressure to obtain 180 mg of desired compound as solid.

$^1$H NMR($CDCl_3$, 200 MHz) δ 2.25(br s, 3H), 2.50–2.99 (m, 3H), 3.65(br s, 2H), 3.60–3.91(m, 2H), 4.09(br s, 3H), 4.05–4.32(m, 1H), 4.55–4.85(m, 2H), 6.35–6.49(m, 1H), 6.81–6.98(m, 1H), 7.01–7.14(m, 1H), 7.20–7.55(m, 4H).

The molecular structure of compounds of Formula I according to the present invention was identified by IR spectrum, IR-Visible spectrum, NMR spectrum, and mass spectrum.

Pyrrolo[3,2-c]quinoline derivatives and their pharmaceutically acceptable salts in which $R_1$ is haloalkoxy group, represented by Formula I, inhibit secretion of the gastric acid reversibly so the pharmaceutical composition which contains them is availably utilized as inhibitor for the gastric acid secretion and therapeutics for gastric ulcer.

Pharmaceutical composition for therapeutics of gastric ulcer having quinoline derivatives and their salts according to the present invention, can be administered orally or non-orally by mixing the compounds of Formula I with generally used nontoxic and pharmaceutically acceptable carrier or diluent.

Pharmaceutical composition of the present invention can be prepared in type of oral administrable forms such as pill; troches; lozenge; water-soluble or oil-soluble suspension; powder or granule; emulsion; hard or soft capsule; syrup; or elixirs.

To prepare the form of pill or capsule, binding agent such as, lactose, saccharose, sorbitol, mannitol, starch, amylopectin, celluose or gelatin; dileunt such as dicalcium phosphate; dissolute such as corn starch or sweet potato starch; lubricant such as magnesium stearate, calcium stearate, sodium stearyl fumarate or polyethylene glycol, etc.

To prepare the form of capsule, liquid carrier like fatty oil can be more included in addition to the above mentioned substance.

Also, pharmaceutical composition containing the compound of Formula I as effective component can be administered non-orally, and by the method of hypodermic injection, intravenous injection, intramuscular injection or intrathoracic injection. By mixing the compound of Formula I or their salts with stabilizer or damping agent in the water, solution or suspension are formed, and ample or vial for unit dosage is prepared by using them for the form of non-oral administration.

Preparation Example 1

Preparation of Syrup

Syrup that contains 2% (wt/vol.) of the quinoline[3,2-c] derivatives or their salts, which contain haloalkoxy group, according to the present invention as effective component is prepared by the process, as follows:

Acid additive salt of pyrrolo[3,2-c]quinoline derivatives having haloalkoxy group, sugar and saccharin was dissolved in 80 g of warm water, and cooled. To prepare the solution, which is consisted of glycerin, saccharin, sweetener and water was prepared, then put into the bottle, and added the water until the volume of solution was 100 ml. Above additive salt can be substituted with another salts of compounds prepared by above Examples.

Here are the components of the syrup.

1-(2-Methylphenyl)-4-[(2-hydroxyethyl)amino]-6-β,β,β-trifluoroethoxy-2,3-dihydropyrrolo[3,2-c]quinoline.HCl

| | |
|---|---|
| salt | 2.0 g |
| Saccharin | 0.8 g |
| Sugar | 25.4 g |
| Glycerin | 8.0 g |
| Sweetener | 0.04 g |
| Ethanol | 4.0 g |
| Sorbic acid | 4.0 g |
| Distilled water | proper volume |

Preparation Example 2
Preparation of Pill

Pill, which contain 15 mg of the above effective component, was prepared by the process, as follows:

250 g of 1-(2-Methylphenyl)-4-[(2-hydroxyethyl)amino]-6-β,β,β-trifluoroethoxy-2,3-dihydropyrrolo[3,2-c]quinoline.HCl salt was mixed with 175.9 g of lactose, 180 g of potato starch and 32 g of colloidal silicate, then added gelatin solution(10%), pulverized, filter with mesh(No. 14), and dried. Hereto was added 160 g of potato starch, 50 g of talc, and 5 g of magnesium stearate to obtain the mixture, and the mixture was prepared in type of pill.

Here are the components of the pill.
1-(2-Methylphenyl)-4-[(2-hydroxyethyl)amino]-6-β,β,β-trifluoroethoxy-2,3-dihydropyrrolo[3,2-c]quinoline.HCl

| | |
|---|---|
| salt | 250.0 g |
| Lactose | 175.9 g |
| Corn starch | 180.0 g |
| Colloidal silicate | 32.0 g |
| 10% Gelatin solution | |
| Potato starch | 160.0 g |
| Talc | 50.0 g |
| Magnesium stearate | 5.0 g |

Preparation Example 3
Preparation of Ampule

Ampule, which contains 10 mg of the above effective component, was prepared by the process, as follows:

1 g of 1-(2-Methylphenyl)-4-[(2-hydroxyethyl)amino]-6-β,β,β-trifluoroethoxy-2,3-dihydropyrrolo[3,2-c]quinoline.HCl salt, 0.6 g of sodium chloride, and 0.1 g ascorbic acid was dissolved in distilled water, and prepared 100 ml of solution. This solution was put into the bottle, and pasteurized by heating at 20° C. for 30 minutes.

Here are the components of the ampule.
1-(2-Methylphenyl)-4-[(2-hydroxyethyl)amino]-6-β,β,β-trifluoroethoxy-2,3-dihydropyrrolo[3,2-c]quinoline.HCl

| | |
|---|---|
| salt | 1.0 g |
| Sodium chloride | 0.6 g |
| Ascorbic acid | 0.1 g |
| Distilled water | proper volume |

Dose of compounds, represented by Formula I, can be different in accordance with the age, weight, gender, severity of disease, health of patient, and type of administration. However, dose of a day is generally preferable 15–25 mg on the basis of adult male.

We performed experiments as following, to confirm the compounds of Formula I have excellent biological effects on inhibiting gastric acid secretion.

Experiment
In Vivo Assay of Pharmacological Activity

Abdomen of SD(Sprague Dawley) male rat(150–200 g) was incised, then the pylorus was ligated, and 20 mg/kg of the solution, obtained by the suspending or dissolving the test compounds in aqueous solution of 30% polyethylene glycol(PEG) 400, was injected in duodenum. After suturing the abdomen and leaving for 5 hours, the rat was euthanized by cerbical dislocation, then ulcer was resected, and gastric juice was collected. After removing the precipitate by centrifugation, the amount and pH of gastric juice was measured, titrated by automatic analyzer "Orion 960", then the effects on inhibiting gastric acid secretion was compared the control and the comparative(SK&F 96067, described in EP 87307824.0 and represented by the following Formula III), with test compounds.

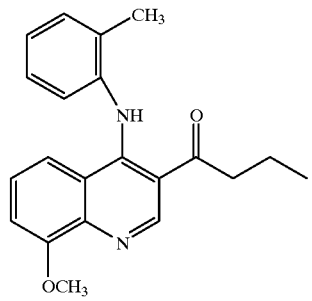

Formula III

In vivo test on enzymatic reaction of $H^+/K^+$-ATPase was carried out, wherein negative control was activity of $H^+/K^+$-ATPase, stimulated by $Mg^{2+}$, and positive control was activity of $H^+/K^+$-ATPase, stimulated by $Mg^{2+}$ and $K^+$, and the result of test was shown in the Table II

TABLE II

| No. | Rate of gastric acid secretion | No. | Rate of gastric acid secretion |
|---|---|---|---|
| 1 | +++ | 41 | + |
| 3 | +++ | 44 | ++ |
| 4 | + | 47 | +++ |
| 5 | + | 48 | +++ |
| 10 | +++ | 49 | +++ |
| 11 | +++ | 55 | +++ |
| 12 | + | 57 | ++ |
| 14 | + | 59 | + |
| 16 | + | 60 | +++ |
| 22 | ++ | 61 | + |
| 26 | +++ | 62 | +++ |
| 28 | +++ | 64 | +++ |
| 32 | + | | |
| 33 | ++ | | |
| 35 | +++ | | |
| 36 | +++ | | |
| HCl salt of 36 | +++ | | |
| 39 | +++ | | |
| 40 | +++ | | |

*Relative pharmaceutical effects to SK&F 96067 (in vivo test)
+++: strong,
++: similar,
+: weak SK&F 96067;
EP 87307824.0

As a result, pyrrolo[3,2-c]quinoline derivatives or their salts having haloalkoxy group could be confirmed that the gastric acid secretion was more excellently inhibited by the compound according to the present invention than by the SK&F 96067, the control.

Pyrrolo[3,2-c]quinoline derivatives and their salts according to the present invention in which $R_1$ is haloalkoxy group show excellent effects on inhibiting gastric acid secretion, as shown in the above Experiments. The compounds of the present invention, which have reversible reaction mechanism of inhibiting gastric acid secretion, are able to solve the problems such as side effects occurred in long term administration the prior irreversible inhibitor, so they are useful for gastric ulcer therapeutics.

What is claimed is:

1. A pyrrolo[3,2-c]quinoline compound or a pharmaceutically acceptable salt thereof having a haloalkoxy group, represented by Formula I

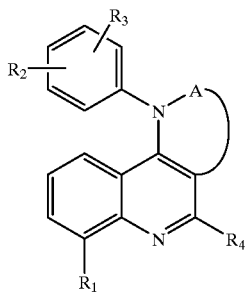

Formula I in which $R_1$ is a haloalkoxy group of $C_1$–$C_6$, $R_2$ and $R_3$, which are the same or different, are each hydrogen, halogen, hydroxy, benzyloxy, alkyl group of $C_1$–$C_6$, or alkoxy group of $C_1$–$C_6$, A is —CH$_2$—CH$_2$— or CH=CH—, and $R_4$ is hydrogen, halogen, amino, alkylamino group of $C_1$–$C_6$, or NH(CH$_2$)$_n$OH in which n is 1–6.

2. A pyrrolo[3,2-c]quinoline compound or a pharmaceutically acceptable salt thereof according to claim 1, wherein $R_1$ is trifluormethoxy, difluoromethoxy or β,β,β-trifluoroethoxy.

3. A pyrrolo[3,2-c]quinoline compound or a pharmaceutically acceptable salt thereof according to claim 2, wherein $R_1$ is β,β,β-trifluoroethoxy.

4. A pyrrolo[3,2-c]quinoline compound or a pharmaceutically acceptable salt according to claim 1 to wherein $R_2$ and $R_3$, the same or different, are respectively hydrogen, methyl, methoxy, hydroxy, or fluoro.

5. A pyrrolo[3,2,-c]quinoline compound or a pharmaceutically acceptable salt thereof according to claim 4, wherein $R_4$ is methylamino, NH(CH$_2$)$_2$OH or NH(CH$_2$)$_3$OH.

6. A compound selected from the groups consisting of the Structures (V), (VI), (VIII) and (IX), useful as an intermediate in the preparation of a pyrrolo[3,2-c]quinoline compound or a pharmaceutically acceptable salt thereof, represented by Formula I in claim 1,

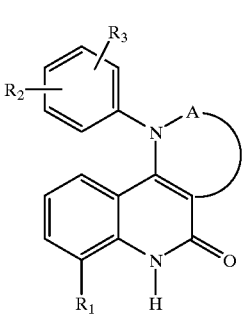

Structure V in which $R_1$, $R_2$, $R_3$ and A are each defined as in Formula I of claim 1, or

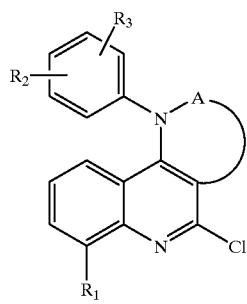

Structure VI in which $R_1$, $R_2$, $R_3$ and A are each defined as in Formula I of claim 1, or

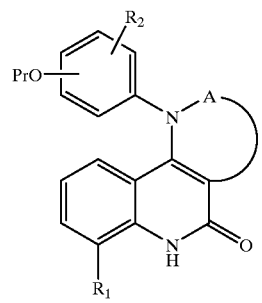

Structure VIII in which $R_1$, $R_2$, $R_3$ and A are each defined as in Formula I of claim 1, and Pr is a hydroxy protecting group,

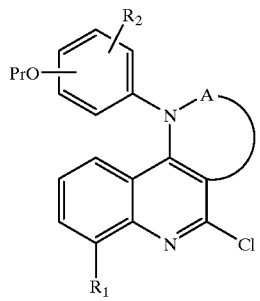

Structure IX in which $R_1$, $R_2$, $R_3$ and A are each defined as in Formula I of claim 1, and Pr is a hydroxy protecting group.

7. A compound of Structure (V) according to claim 6, useful as an for intermediate in the preparation of a pyrrolo[3,2-c]quinoline compound or a pharmaceutically acceptable salt thereof, represented by Formula I, according to claim 1, wherein $R_1$ is trifluoromethoxy, difluoromethoxy or β,β,β-trifluoroethoxy.

8. A compound of Structure (VI) according to claim 6, useful as an intermediate in the preparation of a pyrrolo[3,2-c]quinoline compound or a pharmaceutically acceptable salt thereof, represented by Formula I, according to claim 1, wherein $R_1$ is trifluoromethoxy, difluoromethoxy or β,β,β-trifluoroethoxy.

9. A compounds of Structure (VIII) according to claim 6, useful as an intermediate in the preparation of a pyrrolo[3,2-c]quinoline compound or a pharmaceutically acceptable salt thereof, represented by Formula I, according to claim 1, wherein Pr is methanesulfonyl.

10. A compound of Structure (VIII) according to claim 6, useful as an intermediate in the preparation of a pyrrolo[3,2-c]quinoline compound or a pharmaceutically acceptable salt thereof, represented by Formula I, according to claim 1, wherein $R_1$ is trifluoromethoxy, difluoromethoxy or β,β,β-trifluoroethoxy.

11. A compound of Structure (IX) according to claim 6, useful as an intermediate in the preparation of a pyrrolo[3,2-c]quinoline compound or a pharmaceutically acceptable salt thereof, represented by Formula I, according to claim 1, wherein Pr is methanesulfonyl.

12. A compound of Structure (IX) according to claim 6, useful as an intermediate in the preparation of a pyrrolo[3,2-c]quinoline compound or a pharmaceutically acceptable salt thereof, represented by Formula I, according to claim 1, wherein $R_1$ is trifluoromethoxy, difluoromethoxy or β,β,β-trifluoroethoxy.

13. A pharmaceutical composition of therapeutics for gastric ulcer, which comprises a pyrrolo[3,2-c]quinoline compound or a salt thereof having a haloalkoxy group, represented by Formula I in claim 1, as effective component.

14. A pharmaceutical composition of therapeutics for gastric ulcer according to claim 13, which comprises a pyrrolo[3,2-c]quinoline compound or salt thereof having a haloalkoxy group, represented by Formula I of claim 1, as effective component, wherein $R_1$ is trifluoromethoxy, difluoromethoxy or β,β,β-triflouroethoxy.

15. A pharmaceutical composition of therapeutics for gastric ulcer according to claim 13, which comprises a pyrrolo[3,2-c]quinoline compound or salt thereof having haloalkoxy group, represented by Formula I of claim 1, as effective component, wherein $R_1$ is a β,β,β-triflouroethoxy group.

16. A pyrrolo[3,2-c]quinoline compound or pharmaceutical acceptable salt thereof according to claim 1, wherein $R_1$ is trifluoromethoxy, difluoromethoxy, or trifluoromethoxy.

* * * * *